United States Patent
Cohen et al.

(10) Patent No.: US 10,874,644 B2
(45) Date of Patent: *Dec. 29, 2020

(54) THERAPEUTIC APPROACHES FOR TREATING ALZHEIMER DISEASE AND RELATED DISORDERS THROUGH A MODULATION OF SYNAPSE FUNCTION

(71) Applicant: Pharnext, Paris (FR)

(72) Inventors: Daniel Cohen, Le Vesinet (FR); Ilya Chumakov, Vaux le Penil (FR); Serguei Nabirochkin, Chatenay Malabry (FR); Oxana Guerassimenko, Milly-la-Foret (FR); Nathalie Cholet, Meudon (FR)

(73) Assignee: Pharnext, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/433,097

(22) Filed: Jun. 6, 2019

(65) Prior Publication Data

US 2019/0298698 A1    Oct. 3, 2019

Related U.S. Application Data

(63) Continuation of application No. 14/954,388, filed on Nov. 30, 2015, now Pat. No. 10,350,195, which is a continuation of application No. 12/915,722, filed on Oct. 29, 2010, now abandoned, which is a continuation-in-part of application No. PCT/EP2009/055176, filed on Apr. 29, 2009.

(60) Provisional application No. 61/048,582, filed on Apr. 29, 2008.

(51) Int. Cl.

| | | |
|---|---|---|
| A61K 31/42 | (2006.01) | |
| A61K 31/255 | (2006.01) | |
| A61K 31/155 | (2006.01) | |
| A61K 45/06 | (2006.01) | |
| C07C 279/26 | (2006.01) | |
| C07D 261/20 | (2006.01) | |

(52) U.S. Cl.
CPC ............ *A61K 31/42* (2013.01); *A61K 31/155* (2013.01); *A61K 31/255* (2013.01); *A61K 45/06* (2013.01); *C07C 279/26* (2013.01); *C07D 261/20* (2013.01)

(58) Field of Classification Search
CPC .................................................. A61K 31/42
See application file for complete search history.

(56) References Cited

U.S. PATENT DOCUMENTS

| | | | | |
|---|---|---|---|---|
| 6,342,515 | B1* | 1/2002 | Masuda | A61K 31/42 |
| | | | | 514/379 |
| 6,727,278 | B1* | 4/2004 | Averback | A61K 31/35 |
| | | | | 514/275 |
| 8,552,041 | B2* | 10/2013 | Cohen | A61K 31/4985 |
| | | | | 514/379 |
| 8,809,302 | B2* | 8/2014 | Cohen | A61K 31/137 |
| | | | | 514/56 |
| 9,387,206 | B2* | 7/2016 | Cohen | A61K 31/343 |
| 2004/0102525 | A1 | 5/2004 | Kozachuk | |
| 2008/0188510 | A1 | 8/2008 | Yoshino | |
| 2012/0071483 | A1 | 3/2012 | Cohen et al. | |

FOREIGN PATENT DOCUMENTS

| | | |
|---|---|---|
| EP | 1040830 | 10/2000 |
| WO | WO-2006/110588 A2 | 10/2006 |
| WO | WO-2007/032720 A2 | 3/2007 |

OTHER PUBLICATIONS

Taniguchi et al., Effect of zonisamibe on disturbed behavior in Alzheimer's disease, International Clinical Psychopharmacology, Jan. 1998, vol. 18, issue 1, p. 43.*

Rossor et al., Neurochemical characteristics of early and late onset types of Alzheimer's disease, Br Med J (Clin Res Ed). Mar. 31, 1984;288(6422):961-4.*

Levin et al., Baclofen interactions with nicotine in rats: effects on memory, Pharmacology, Biochemistry and Behavior 79 (2004) pp. 343-348.*

Kawas et al "Alzheimer's and Dementia in the Oldest-Old: A Century of Challenges" Current Alzheimer Research vol. 3, pp. 411-419, 2006.

Lee et al "Phenformin Suppresses Calcium Responses to Glutamate and Protects Hippocampal Neurons Against Excitotoxicity" Experimental Neurology vol. 175, pp. 161-167, 2002.

Rautio et al "Prodrugs: Design and Clinical Applications" Nature Reviews Drug Discovery vol. 7, pp. 255-270, 2008.

Taniguchi et al "Effect of Zonisamibe on Distributed Behavior in Alzheimer's Disease" International Clinical Psychopharmacology vol. 18, p. 43, 1998.

Van Sickle et al "Inhibition of Cholesterol Synthesis by Cyclopropylamine Derivatives of Squalene in Human Hepatoblastoma Cells in Culture" Lipids vol. 27, pp. 157-160, 1992.

\* cited by examiner

*Primary Examiner* — Svetlana M Ivanova

(74) *Attorney, Agent, or Firm* — Cesari & McKenna, LLP

(57) ABSTRACT

Compositions and methods for the treatment of Alzheimer's disease and related disorders. More particularly, disclosed are combined therapies that modulate synapse function for treating the disease.

7 Claims, 3 Drawing Sheets

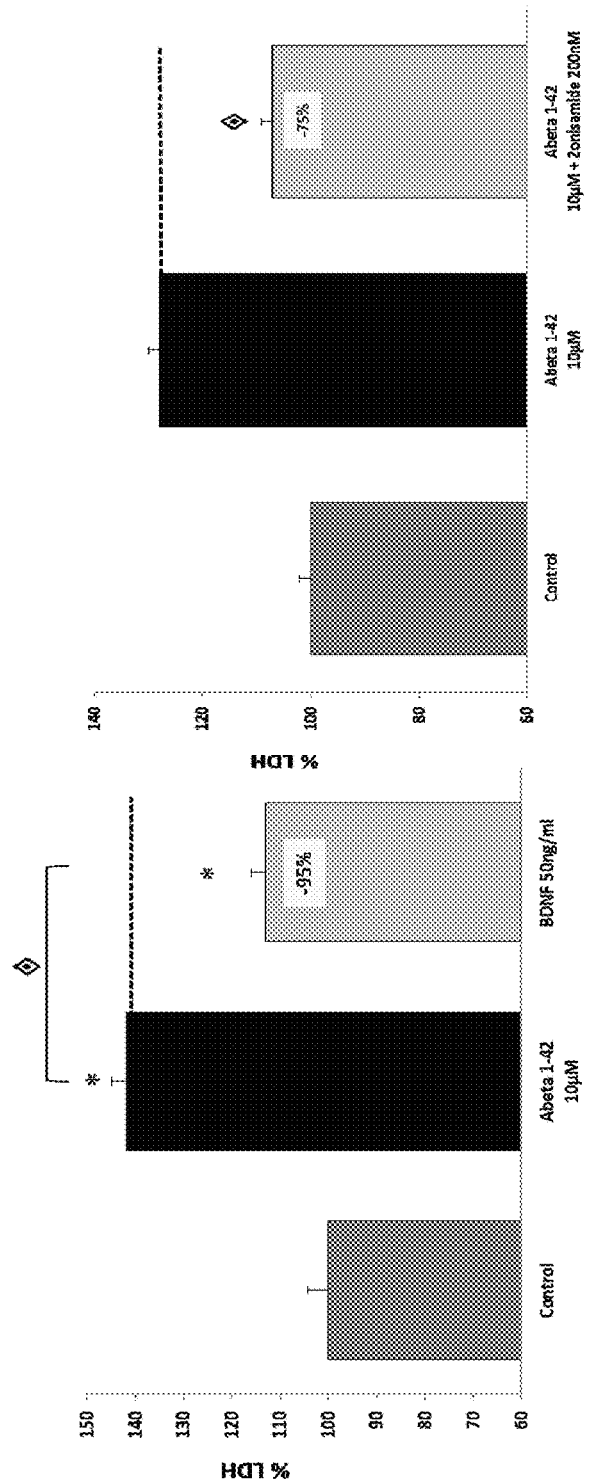
FIG. 3A
FIG. 3B
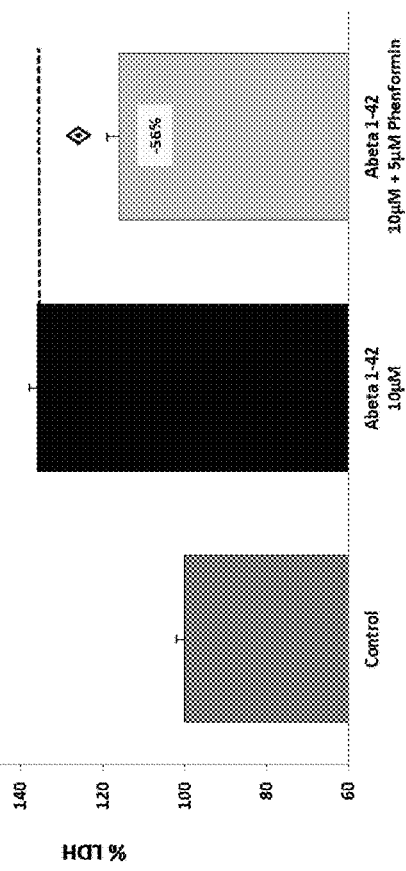
FIG. 3C

THERAPEUTIC APPROACHES FOR TREATING ALZHEIMER DISEASE AND RELATED DISORDERS THROUGH A MODULATION OF SYNAPSE FUNCTION

CROSS REFERENCE TO RELATED APPLICATION

This application is a continuation of copending U.S. patent application Ser. No. 14/954,388, filed on Nov. 30, 2015, which is a continuation of U.S. patent application Ser. No. 12/915,722, filed on Oct. 29, 2010, which is a continuation-in-part of International Application No. PCT/EP2009/055176, filed on Apr. 29, 2009, which claims priority of U.S. Provisional Application No. 61/048,582, filed on Apr. 29, 2008. The contents of all of the foregoing applications are hereby incorporated by reference in their entirety.

BACKGROUND

The present invention relates to compositions and methods for the treatment of Alzheimer's disease (AD) and related disorders.

AD is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved (1-4).

Incidence of Alzheimer disease increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (5).

The incidence rate of AD increases dramatically with age. United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources (6).

Memory impairment is the early feature of the disease and involves episodic memory (memory for day-today events). Semantic memory (memory for verbal and visual meaning) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of Alzheimer's disease is sufficiently characteristic to allow identification in approximately 80% of cases (7). Nevertheless, clinical heterogeneity does occur and not only is this important for clinical management but provides further implication of specific medication treatments for functionally different forms. (8).

The pathological hallmark of AD includes amyloid plaques containing beta-amyloid (Abeta), neurofibrillary tangles (NFT) containing Tau and neuronal and synaptic dysfunction and loss (9-11). For the last decade, two major hypotheses on the cause of AD have been proposed: the "amyloid cascade hypothesis", which states that the neurodegenerative process is a series of events triggered by the abnormal processing of the Amyloid Precursor Protein (APP) (12), and the "neuronal cytoskeletal degeneration hypothesis" (13), which proposes that cytoskeletal changes are the triggering events. The most widely accepted theory explaining AD progression remains the amyloid cascade hypothesis (14-16) and AD researchers have mainly focused on determining the mechanisms underlying the toxicity associated with Abeta proteins. On contrary, Tau protein has received much less attention from the pharmaceutical industry than amyloid, because of both fundamental and practical concerns. Moreover, synaptic density change is the pathological lesion that best correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals (11).

SUMMARY

The purpose of the present invention is to provide new therapeutic approaches for treating AD and related disorders.

The inventors have identified a molecular pathway which is involved in the genesis of AD and offers novel targets for development of new treatments to ameliorate AD and related disorders, particularly for the development of combination therapies using novel or existing molecules previously used in other indications. More particularly, the inventors have identified several drugs which, alone or in combination(s), can effectively affect such pathway and represent a new and effective therapy for the treatment of AD and related disorders.

The invention therefore provides novel compositions and methods for treating AD disease and related disorders.

More particularly, the invention relates to compositions suitable for treating Alzheimer's disease or a related disorder in a subject in need thereof, wherein said compositions comprise a drug that ameliorates synapse function.

A further object of this invention relates to compositions suitable for treating Alzheimer's disease or a related disorder in a subject in need thereof, wherein said compositions comprise a combination of at least two drugs that ameliorate synapse function, for combined, separate or sequential administration.

More preferably, the drug or drugs that ameliorate synapse function bind to or modulate the activity of a protein encoded by a gene selected from ABAT, ABI1, ABL1, ADORA2A, ADORA2B, AKT, AMPK, ANKRA, APBA1, ARHGAP26, ATG5, BASSOON, BDNF, BECLIN1, BIN1, BK channels (KCNMA1, KCNMB1), CACNA1C, CACNA2D3, CACNA2D4, CADPS2, CALCINEURIN, CALMODULIN, CASK, CASR, CAST, CBL, CDC2, CDC42, CDC42BPB, CDC42EP3, CDH13, CDH2, CDK5, CITRON, CNGB3, CORTACTIN, CRAM, CREB, CRMP, CTNNB1, DAB1, DCC, DEPDC2, DHFR, DLG2, DYN1, DYN3, EDNRA, ENDOPHILIN, EPHA3, EPHBR, EPHEXIN, EPHRINA, EPHRINB, ERBB4, ERK1, ERK2, FES, FYN, GABBR1, GABBR2, GABRA2, GABRG2, GAT1, GLRA1, GEPHYRIN, GIPC1, GIPC2, GLUD1, GRANUPHILIN, GRIA2, GRIA3, GRID1, GRID2, GRIK1, GRIK2, GRIN2B, GRIN3A, GRIP, GRM3, GRM5, GRM6, GRM7, GRM8, HOMER, HTR1B, HTR1D, KALIRIN, KCNA2, KCHIP1, KCHIP2.2, KCND2, KCNJ3, KCNJ12, KTN1, KYNU, LYN, MAML3, MINT1, MUC1, MUNC13, MUNC18A, MYO6, MYOL, NAV1, NBEA, NCAM1, NCK1, NCK2, NETRIN1, NFKB1, NGEF, NGF, NGFR, NIL16, NLGN1, NOC2, NOS1, NOTCH1, NOTCH2, NOTCH3, NPC1, NPC2, NPIST, NRG3, NRP1, NRP2, NRX3, NTF3, NTF5, NWASP, OPCML, OPRK1, PAK6, PAK7, PAR1, PARK2, PDE11A, PDE3A/3B, PDE4A/4B/4D, PI3K, PIAS1, PICALM, PICK1, PIP5K, PKA, PKCA, PLD2, PLEXA1, PP1C, PPFIBP1, PRKG1, PSD95, PTN, PTPRF, PYK2, RAB3B, RABPHILIN, RAC1, RAP1, RAS, RASGRF2, RBPJ, REELIN, RGNEF, RHOA, RHOG, RIM2, RIMS1, RIMS2, ROBO2, ROCK2, RPH3AL, SACM1L, SAPAP, SCN1A, SCN1B, SEC24D, SEMA3A, SEMA3C, SEMA3E, SEMA4C, SIAH1A, SLC12A1, SLC12A2, SLC12A5, SLC1A2, SLC6A1, SLC6A18, SLC9A1, SLIT1, SNAP25, SORBS2, SRC, SRGAP3, STX2, STXBP6, SUM1, SV2C, SYNAPTOJANIN, SYNTAXIN1A, SYT12, TACE, TBR1, TRIO, TRKB, TROMBIN, TSPO, UBE2A, ULK4, UNC13C, UNC5C, VAMP2, VAMPS, VELI, VINCULIN, WASPIP, WAVE, WWOX, YAP, and YES1.

Specific and preferred examples of such drugs include, without limitation, compounds selected from acamprosate, alendronate, alfentanil, amiloride, amlodipine, argatroban, aztreonam, baclofen, buclizine, bumetanide, buprenorphine, lidocaine, chlorzoxazone, cilostazol, cinacalcet, dasatinib, desirudin, dyphylline, eletriptan, ergotamine, flunitrazepam, fosphenytoin, imatinib, ketotifen, milrinone, nitroprusside, pegaptanib, pentazocine, phenobarbital, phenformin pregabalin, propylthiouracil, sulfisoxazole, tadalafil, temazepam, terbinafine, tiagabine, topiramate, triamterene, vigabatrin and zonisamide, or a combination thereof.

In a particular embodiment, the compositions of this invention further comprise at least one drug that modulates angiogenesis, for combined, separate or sequential use.

Alternatively, or in addition, the compositions of this invention may further comprise at least one drug that modulates cell stress response, for combined, separate or sequential use.

The compositions of this invention typically further comprise a pharmaceutically acceptable carrier or excipient.

A further object of this invention resides in a method of producing a drug for treating Alzheimer's disease or a related disorder, the method comprising a step of testing a candidate drug for activity on synapse function and selecting candidate drugs that ameliorate synapse function.

The invention also relates to a method of producing a composition for treating Alzheimer's disease or a related disorder, the method comprising preparing a combination of a drug that modulates synapse function and a drug that modulates angiogenesis or cell stress response, and formulating said combination of drugs for simultaneous, separate or sequential administration thereof to a subject in need thereof.

The invention further relates to a method of treating Alzheimer's disease or a related disorder, the method comprising simultaneously, separately or sequentially administering to a subject in need thereof a drug or a combination of drugs that ameliorate synapse function.

The invention further relates to a method of treating Alzheimer's disease or a related disorder, the method comprising simultaneously, separately or sequentially administering to a subject in need thereof a drug that modulates synapse function and a drug that modulates angiogenesis and/or a drug that modulates cell stress response.

The invention further relates to the use of a drug that ameliorates synapse function for the manufacture of a medicament for treating Alzheimer's disease or a related disorder.

The invention further relates to the use of a combination of at least two drugs that ameliorate synapse function for the manufacture of a medicament for treating Alzheimer's disease or a related disorder, wherein said at least two drugs are administered together, separately or sequentially.

As discussed in the present application, the above therapies and combination therapies provide novel and effective approaches for treating AD in human subjects.

BRIEF DESCRIPTION OF THE DRAWINGS

FIG. 3A: Effect of BDNF pre-treatment on LDH release in human $A\beta_{1-412}$ toxicity on rat primary cortical cells. $A\beta_{1-42}$ produces a significant intoxication compared to vehicle-treated neurons. 1 h of BDNF (50 ng/ml) pre-treatment significantly protected the neurons from this amyloid injury (positive control). *: $p<0.05$: significantly different from control (no intoxication); ◆: $p<0.05$: significantly different from Amyloid intoxication (ANOVA+Dunett Post-Hoc test).

FIG. 3B: Effect of zonisamide pre-treatment on LDH release in human $A\beta_{1-42}$ toxicity on rat primary cortical cells. The intoxication is significantly prevented by zonisamide (−75%). ◆: $p<0.05$: significantly different from $A\beta_{1-42}$ intoxication (ANOVA+Dunett Post-Hoc test).

FIG. 3C: Effect of phenformin pre-treatment on LDH release in human $A\beta_{1-42}$ toxicity on rat primary cortical cells. The intoxication is significantly prevented by phenformin (−56%). ◆: $p<0.05$: significantly different from $A\beta_{1-42}$ intoxication (ANOVA+Dunett Post-Hoc test).

DETAILED DESCRIPTION

Figures 1A, 1B:
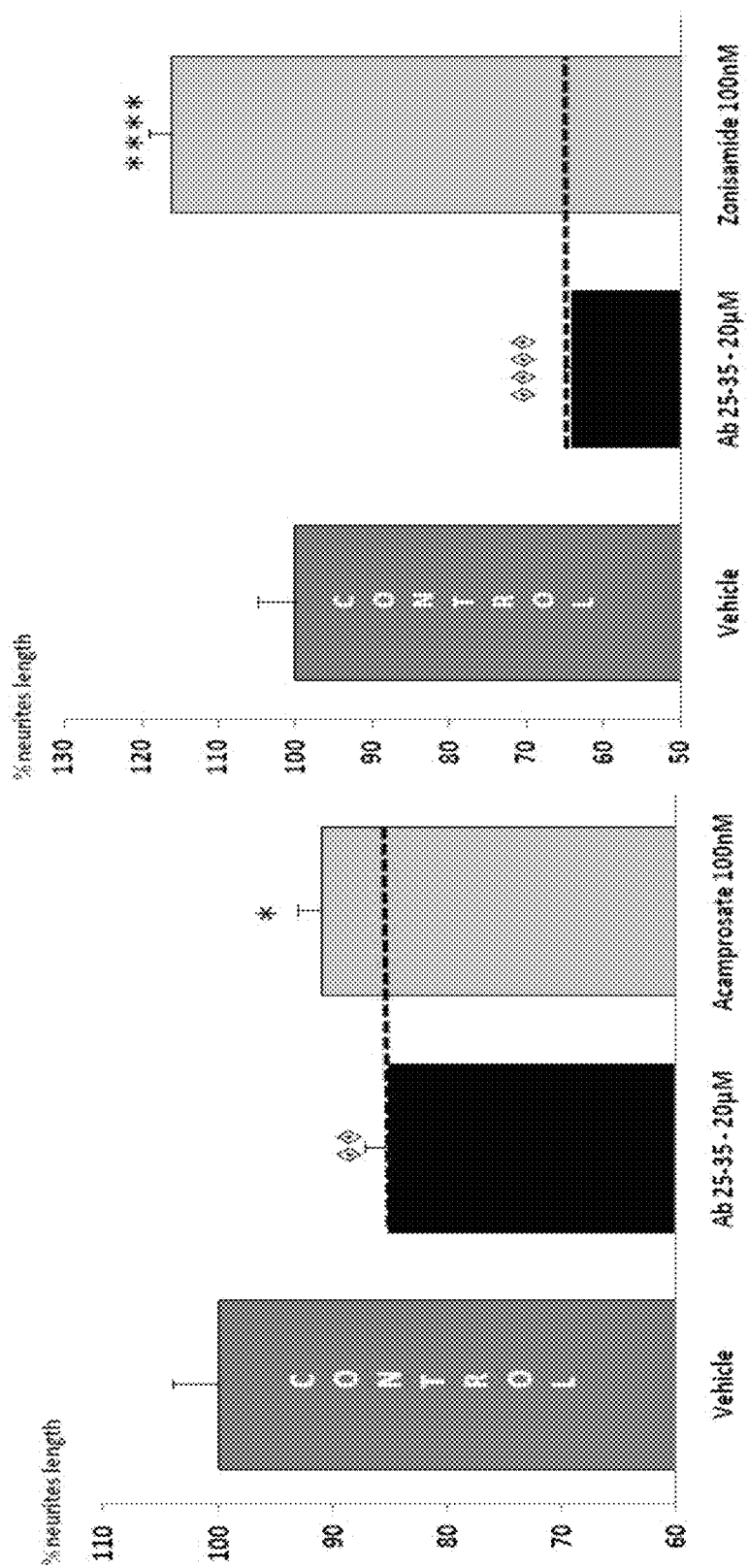
FIG. 1A: Effect of acamprosate on neurite outgrowth in beta-amyloid intoxicated rat primary cortical neuron culture. $A\beta_{25-35}$ 20 µM produces a significant intoxication, above 25%, compared to vehicle-treated neurons. This intoxication is significantly prevented by acamprosate. ◆◆: $p<0.01$; *:$p<0.05$: significantly different from $Abeta_{25-35}$, Bilateral Student's t test.
FIG. 1B: Effect of zonisamide on neurite outgrowth in beta-amyloid intoxicated rat primary cortical neuron culture. $A\beta_{25-35}$ 20 µM produces a significant intoxication, above 25%, compared to vehicle-treated neurons. This intoxication is significantly prevented by zonisamide. ◆◆◆◆: $p<0.00001$; ****:$p<0.0001$: significantly different from $Abeta_{25-35}$. Bilateral Student's t test.

The present invention provides new therapeutic approaches for treating AD or related disorders. The invention discloses novel use of drugs or drug combinations which allow an effective correction of such diseases and may be used for patient treatment.

The term "AD related disorder" designates Alzheimer's disease (AD), senile dementia of AD type (SDAT), Parkinson's disease, Lewy body dementia, vascular dementia, mild cognitive impairment (MCI), age-associated memory impairment (AAMI) and problem associated with ageing, post-encephalitic Parkinsonism, ALS and Down syndrome.

As used herein, "treatment" of a disorder includes the therapy, retardation, or reduction of symptoms provoked by the disorder. The term treatment includes in particular the control of disease progression and associated symptoms.

The term "ameliorate", as it refers to synapse function, includes any increase in the synapse function as compared to the existing function in the subject. Such amelioration may include a restoration, i.e., to normal levels, or lower increase, which are still sufficient to improve the patient condition. Such an amelioration can be evaluated or verified using known biological tests, such as described in the experimental section.

Also, the designation of specific compounds within the context of this invention is meant to include not only the specifically named molecules, but also any pharmaceutically acceptable salt, hydrate, ester, ether, isomers, racemate, conjugates, or pro-drugs thereof.

The term "combination" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

As discussed above, the invention relates to compositions and methods for treating Alzheimer's disease or a related disorder in a subject in need thereof, using a drug or a combination of drugs that ameliorate synapse function.

By a comprehensive integration of experimental data covering results of cell biology studies, expression profiling experiments and genetic association studies, describing different aspects of Alzheimer's disease and links existing in cellular signalling and functional pathways, the inventors have uncovered that synapse function represents a important mechanism which is altered in subjects having AD. Genes located in said functional network and implicated in Alzheimer's disease were selected by the following criteria:
  (1)—direct interaction with the genes causatively responsible for familial cases of Alzheimer's disease (APP, ApoE, presenilins, tau protein),
  (2)—functional partners of the genes selected by the criterion (1),
  (3)—nearest functional partners of the genes selected by the criterion (2).

Through this process, the inventors were able to establish that the network responsible for synapse dysfunction is a major functional network affected in Alzheimer's disease.

The inventors have more specifically established that the synaptic loss is a functionally-relevant hallmark of Alzheimer's disease, which ultimately leads to progressive cognitive decline, memory loss and dementia. Importantly, synaptic loss correlates better with cognitive deficit characterized Alzheimer's pathology, compared to other AD-specific cellular lesion markers manifested in development of neurofibrillary tangles or deposition of amyloid plaques. Consequently, synapse organization and synaptic plasticity represent an important target for therapeutic interventions in the context of Alzheimer's disease.

APP protein is axonally transported and processed in presynaptic terminals, leading to high accumulation of Abeta at synapses. Oligomers of Abeta42 as well as amyloid plaques themselves are important for inhibiting long-term potentiation and are primarily responsible for memory impairment in AD patients.

Our data integration procedure revealed a group of genes, which are implicated in synaptic distortion in AD and which can be formally separated into three main functional groups: proteins participating in organization of post-synaptic density ("PSD") and correct nerve signal transmission at post-synaptic membrane; proteins assuring neurotransmitter release; and proteins involved in axon growth and developmental maturation of synaptic machinery.

In a particular embodiment, the present invention thus relates to compositions and methods using drugs that ameliorate the activity of proteins involved in post-synaptic density.

The afferent part of excitatory synapses - Post Synaptic Density - are composed of a tightly integrated network of scaffold proteins and neurotransmitter receptors that serve a wide range of cognitive functions, including memory formation and learning.

Among genes identified by our analysis, the DLG2 gene encodes MAGUK family protein that creates an interface between clustered membrane-bound receptors, cell-adhesion molecules and actin-based cytoskeleton. We also identified a large group of glutamate and growth factor receptors, which interact directly with the DLG2 protein or DLG2/PSD95 proteins complex at excitatory synapses—namely, ErbB4 and TrkB receptors processed and functionally regulated by presenilin (17-18), ionotrophic glutamate receptors of kainate (GRIK2) and NMDA types (GRIN3A, GRIN2B), delta type (GRID1, GRID2) glutamate receptors, and G-protein- coupled metabotropic glutamate receptors (GRM3, GRM7, and GRM8). As well, we identified several effector/modulator proteins that are involved in downstream signalling of the synaptic receptors—citron, a Rho/Rac effector protein, RAS GRF2 linking AMPA receptors to activation of RAS/ERK kinases, PARK2 and YES1 kinase.

Other AD-relevant functionally important genes revealed by our analysis include presynaptic γ-Neurexin (NXR3) and postsynaptic neuroligin1 (NLGN1) proteins that form functional complex involved in dynamic co-regulation of pre- and postsynaptic membranes at excitatory synapses.

In general, the population of PSD proteins potentially implicated in Alzheimer's disease is enriched by receptors participating in organization of excitatory glutamatergic synapses; only a few inhibitory neuronal receptors—GABA (A) and GABA(B)—were detected by our data mining screen.

In another particular embodiment, the present invention relates to compositions and methods using drugs that ameliorate the activity of proteins involved in the regulation of neurotransmitter release, preferably at the pre-synaptic membrane.

The release of neurotransmitters at a restricted and highly specialized active zone of the presynaptic plasma membrane is triggered by action potential and is controlled by combined and opposite actions of voltage-dependent, calcium-selective $Ca_v$ channels (positive modulators of neurotransmitter release) and of MaxiK channels, large conductance, voltage and calcium-sensitive potassium channels (negative modulators of neurotransmitter release). Both types of channels were selected by our analysis as pertinent therapeutic targets for treatment of Alzheimer's disease. Additionally, neurotransmitter release at presynaptic membrane could be modulated by simultaneous application of drugs influencing activity of the PRKG1 kinase and/or presynaptic GABA(B) receptors.

Our analysis revealed also a group of proteins involved in structural organization of neurotransmitter release machinery, responsible for maturation, docking and fusion of synaptic vesicle with the proteins composing an active zone— STX2 and STXBP6 proteins participating in synaptic vesicle fusion, BIN1, RAB3B, UNC13C protein essential for the maturation and priming of synaptic vesicles, and RIMS1/2 scaffolding proteins. The proteins identified by our analysis represent both structural proteins, directly involved in exocytosis/endocytosis and recycling of synaptic vesicles, and their functional activity-dependent modulators.

In another particular embodiment, the present invention relates to compositions and methods using drugs that ameliorate the activity of proteins involved in the regulation of axon growth and guidance.

Proteins participating in regulation of axon growth and guidance allow neuronal precursor cells and axons to migrate toward proper destinations to ensure correct location and connectivity; they are also involved in developmental maturation of newly established synapses as well as degradation of axons and synopsis in AD disease. These processes play a fundamental role for execution of cognitive functions and seem to be extremely vulnerable to toxic effect of Abeta depositions.

Consecutive steps of axon growth and guidance are tightly controlled by combined actions of extracellular or membrane-tethered Netrins, Semaphorins, Ephrins, DLL and Slits molecules and their respective functional receptors, most of which were revealed by our data mining approach. Functional outcomes of activation of most of axon growth receptors are tightly connected with their ability to differentially modulate activity of small GTPases RhoA, Rac1 and Cdc42, with the RhoA GTPase being mainly responsible for neurite retraction and growth cone collapse (19).

Among selected genes, DCC axon guidance Netrin receptor is involved both in neurons attraction and repulsion, while UNC5C netrin receptor rather possesses neuron repulsion activity (20); semaphorins and ephrins mediate growth cones collapse and repulsion in nervous system during development and play an important role in synaptic plasticity in adult CNS (21-25). Slits proteins are involved simultaneously to axons repulsion and branching, two tightly linked processes, and modulate activity of netrin receptors (26). Finally, Notch receptor seems to affect axon guidance through both RBPJ-dependent and RBPJ-independent ABL1/DAB1/TRIO pathway controlling organization of actin cytoskeleton (27).

In the present invention, the inventors propose novel compositions, which can be used to ameliorate synapse function altered in Alzheimer's disease and other neurogenerative disorders. In a particular embodiment, the compositions and methods of this invention use drugs that ameliorate synapse function through their interaction with or modulation of one gene or protein as listed above.

More specifically, the compositions of this invention comprise a drug or drugs that ameliorate synapse function through binding to or modulating the activity of a protein encoded by a gene selected from ABAT, ABI1, ABL1, ADORA2A, ADORA2B, AKT, AMPK, ANKRA, APBA1, ARHGAP26, ATG5, BASSOON, BDNF, BECLIN1, BIN1, BK channels (KCNMA1, KCNMB1), CACNA1C, CACNA2D3, CACNA2D4, CADPS2, CALCINEURIN, CALMODULIN, CASK, CASR, CAST, CBL, CDC2, CDC42, CDC42BPB, CDC42EP3, CDH13, CDH2, CDK5, CITRON, CNGB3, CORTACTIN, CRAM, CREB, CRMP, CTNNB1, DAB1, DCC, DEPDC2, DHFR, DLG2, DYN1, DYN3, EDNRA, ENDOPHILIN, EPHA3, EPHBR, EPHEXIN, EPHRINA, EPHRINB, ERBB4, ERK1, ERK2, FES, FYN, GABBR1, GABBR2, GABRA2, GABRG2, GAT1, GLRA1, GEPHYRIN, GIPC1, GIPC2, GLUD1, GRANUPHILIN, GRIA2, GRIA3, GRID1, GRID2, GRIK1, GRIK2, GRIN2B, GRIN3A, GRIP, GRM3, GRM5, GRM6, GRM7, GRM8, HOMER, HTR1B, HTR1D, KALIRIN, KCNA2, KCHIP1, KCHIP2.2, KCND2, KCNJ3, KCNJ12, KTN1, KYNU, LYN, MAML3, MINT1, MUC1, MUNC13, MUNC18A, MYO6, MYOL, NAV1, NBEA, NCAM1, NCK1, NCK2, NETRIN1, NFKB1, NGEF, NGF, NGFR, NIL16, NLGN1, NOC2, NOS1, NOTCH1, NOTCH2, NOTCH3, NPC1, NPC2, NPIST, NRG3, NRP1, NRP2, NRX3, NTF3, NTF5, NWASP, OPCML, OPRK1, PAK6, PAK7, PAR1, PARK2, PDE11A, PDE3A/3B, PDE4A/4B/4D, PI3K, PIAS1, PICALM, PICK1, PIP5K, PKA, PKCA, PLD2, PLEXA1, PP1C, PPFIBP1, PRKG1, PSD95, PTN, PTPRF, PYK2, RAB3B, RABPHILIN, RAC1, RAP1, RAS, RASGRF2, RBPJ, REELIN, RGNEF, RHOA, RHOG, RIM2, RIMS1, RIMS2, ROBO2, ROCK2, RPH3AL, SACM1L, SAPAP, SCN1A, SCN1B, SEC24D, SEMA3A, SEMA3C, SEMA3E, SEMA4C, SIAH1A, SLC12A1, SLC12A2, SLC12A5, SLC1A2, SLC6A1, SLC6A18, SLC9A1, SLIT1, SNAP25, SORBS2, SRC, SRGAP3, STX2, STXBP6, SUM1, SV2C, SYNAPTOJANIN, SYNTAXIN1A, SYT12, TACE, TBR1, TRIO, TRKB, TROMBIN, TSPO, UBE2A, ULK4, UNC13C, UNC5C, VAMP2, VAMPS, VELI, VINCULIN, WASPIP, WAVE, WWOX, YAP, and YES1.

The sequences of all of the above listed genes and proteins are available from gene libraries and can be isolated by techniques known in the art. Furthermore, the activity of these genes and proteins can be assessed by techniques known per se in the art, as discussed in the experimental section.

The invention further describes drugs that can be used to modulate these target genes and proteins. The invention discloses the identification and activity of particular drugs which, either alone but preferentially in combination(s), modulate the above pathway and may be used to treat said diseases. In particular, we identified small molecules which already exist in the literature but being used to treat distinct diseases in human subjects.

In this respect, in a most preferred embodiment, the compositions of this invention comprise at least an inhibitor of ABAT (preferably, vigabatrin); and/or an inhibitor of ABL1 (preferably imatinib); and/or a modulator of ADORA2B (preferably dyphylline); and/or a modulator of AMPK (preferably phenformin) and/or an inhibitor of CACNA1C (preferably amlodipine); and/or an inhibitor of CACNA2D3 (preferably pregabalin); and/or a modulator of CASR (preferably cinacalcet) ; and/or a modulator of CNGB3 (preferably amiloride), and/or an inhibitor of DHFR (preferably triamterene), and/or an inhibitor of EPHA3 (preferably dasatinib), and/or antagonist of EDNRA endothelin receptor (preferably sulfisoxazole), and/or a modulator of GABBR2 and glutamatergic receptors (preferably selected from baclofen and acamprosate), and/or a modulator of GABRA2 (preferably selected from phenobarbital and aztreonam), and/or an antagonist of GRIK1 (preferably, topiramate), and/or a modulator of GRIN2B and GRIN3A (preferably, acamprosate), and/or a modulator of HTR1B and HTR1D (preferably selected from ergotamine and eletriptan), and/or an antagonist of KCND2 (preferably, lidocaine), and/or a modulator of KCNMA1 (preferably, chlorzoxazone), and/or a modulator of NOS1 (preferably selected from ketotifen and propylthiouracil), and/or an inhibitor of NRP2 (preferably, pegaptanib), and/or a modulator of OPCML (preferably, alfentanil), and/or a modulator of OPRK1 (preferably selected from buprenorphine and pentazocine), and/or an inhibitor of trombin receptor PAR1 (preferably, argatroban), and/or an inhibitor of PDE11A and PDE4A, PDE5A phosphodiesterases (preferably, tadalafil), and/or an inhibitor of PDE3A/3B and PDE4A/4B phosphodiesterases and an activator of BK channels (preferably, cilostazol), and/or an inhibitor of PDE4D (preferably, milrinone), and/or an activator of PRKG1 (preferably selected from nitroprusside, tadalafil and cilostazol), and/or a modulator of RHOA (preferably selected from alendronate and terbinafine), and/or an inhibitor of sodium channel SCN1A and an activator of BK channels (preferably, zonisamide), and/or an inhibitor of SCN1A/B (preferably, fosphenytoin), and/or an inhibitor of SLC6A1 (preferably, tiagabine), and/or a modulator of SLC9A1 (preferably, buclizine), and/or an inhibitor of SLC12A1 (preferably, bumetanide), and/or an inhibitor of TROMBIN (preferably, desirudin), and/or a modulator of TSPO (preferably selected from flunitrazepam and temazepam), and/or an inhibitor of YES1 (preferably, dasatinib).

As discussed above, the invention particularly proposes to design combination therapies to address the mechanisms of AD and related disorders. In this respect, examples of most preferred target and drug combinations are disclosed below.

More preferably, the composition of the invention comprises at least one of the following combinations of drugs, for combined, separate or sequential administration:

a modulator of AMPK (preferably, phenformin) and an inhibitor of sodium channel SCN1A and an activator of BK channels (preferably, zonisamide), a modulator of AMPK (preferably, phenformin) and a modulator of GABAergic and glutamatergic receptors (preferably, acampro sate), a modulator of AMPK (preferably, phenformin) and an antagonist of EDNRA endothelin receptor (preferably, sulfisoxazole), a modulator of GABAergic and glutamatergic receptors (preferably, acamprosate) and an antagonist of EDNRA endothelin receptor (preferably, sulfisoxazole), an inhibitor of sodium channel SCN1A and an activator of BK channels (preferably, zonisamide) and an antagonist of EDNRA endothelin receptor (preferably, sulfisoxazole).

a modulator of GABAergic and glutamatergic receptors (preferably, acamprosate) and an inhibitor of PDE3A/3B and PDE4A/4B phosphodiesterases and an activator of BK channels (preferably, cilostazol), an inhibitor of sodium channel SCN1A and an activator of BK channels (preferably, zonisamide) and a modulator of adenosine receptor ADORA2B (preferably, dyphylline), an inhibitor of sodium channel SCN1A and an activator of BK channels (preferably, zonisamide) and an inhibitor of trombin receptor PAR1 (preferably, argatroban), a modulator of AMPK (preferably, phenformin) and a modulator of adenosine receptor ADORA2B (preferably, dyphylline), a modulator of AMPK (preferably, phenformin) and an inhibitor of PDE3A/3B and PDE4A/4B phosphodiesterases and an activator of BK channels (preferably, cilostazol), an inhibitor of sodium channel SCN1A and an activator of BK channels (preferably, zonisamide), a modulator of GABAergic and glutamatergic receptors (preferably, acamprosate), an inhibitor of PDE11A and PDE4A, PDE5A phosphodiesterases (preferably, tadalafil) and an inhibitor of PDE3A/3B and PDE4A/4B phosphodiesterases and an activator of BK channels (preferably, cilostazol), or an inhibitor of sodium channel SCN1A and an activator of BK channels (preferably, zonisamide) and an inhibitor of PDE3A/3B and PDE4A/4B phosphodiesterases and an activator of BK channels (preferably, cilostazol).

Most preferred examples of compositions of this invention comprise a compound selected from acamprosate, alendronate, alfentanil, amiloride, amlodipine, argatroban, aztreonam, baclofen, buclizine, bumetanide, buprenorphine, lidocaine, chlorzoxazone, cilostazol, cinacalcet, dasatinib, desirudin, dyphylline, eletriptan, ergotamine, flunitrazepam, fosphenytoin, imatinib, ketotifen, milrinone, nitroprusside, pegaptanib, pentazocine, phenformin, phenobarbital, pregabalin, propylthiouracil, sulfisoxazole, tadalafil, temazepam, terbinafine, tiagabine, topiramate, triamterene, vigabatrin and zonisamide, or a combination thereof.

Most preferred examples of combination therapies of this invention comprise the combined use of at least the following compounds:
phenformin and zonisamide,
phenformin and acamprosate,
phenformin and sulfisoxazole,
acamprosate and sulfisoxazole,
zonisamide and sulfisoxazole,
acamprosate and zonisamide,
acamprosate and cilostazol,
zonisamide and dyphylline,
zonisamide and argatroban,
phenformin and dyphylline,
phenformin and cilostazol,
tadalafil and cilostazol,
zonisamide and cilostazol,
phenformin and tadalafil, or
zonisamide and terbinafine.

Most preferred compositions of this invention comprise at least one compound chosen from the group consisting of zonisamide, dyphylline, tadalafil, argatroban, acamprosate, cinacalcet, terbinafine, cilostazol, baclofen, phenformin, amlodipine and sulfisoxazole, or salts or prodrugs or derivatives or sustained release formulations thereof.

In the most preferred embodiment, the compositions according to the invention, comprise zonisamide, or a salt or a prodrug or a derivative or a sustained release formulation thereof, for treating Alzheimer's disease (AD) in a subject in need thereof.

In a more preferred embodiment, the compositions of the invention comprise a combination of at least two compounds chosen from the group consisting of zonisamide, dyphylline, tadalafil, argatroban, acamprosate, cinacalcet, terbinafine, cilostazol, baclofen, phenformin, amlodipine and sulfisoxazole, or salts or prodrugs or derivatives or sustained release formulations thereof, for simultaneous, separate or sequential administration.

In another embodiment, the composition according to the invention comprises a combination of at least two compounds chosen from the group consisting of zonisamide, dyphylline, tadalafil, argatroban, acamprosate, cinacalcet, terbinafine, cilostazol, baclofen, phenformin, amlodipine and sulfisoxazole, or salts or prodrugs or derivatives or sustained release formulations thereof, wherein said composition ameliorates synapse function altered in neurodegenerative disorders selected from the group consisting of Alzheimer's disease (AD), Parkinson's disease (PD), Amyotrophic lateral sclerosis (ALS) and multiple sclerosis (MS).

In another preferred embodiment, the composition of the invention comprises a combination of at least two compounds chosen from the group consisting of zonisamide, dyphylline, tadalafil, argatroban, acamprosate, cinacalcet, terbinafine, cilostazol, baclofen, phenformin, amlodipine and sulfisoxazole, or salts or prodrugs or derivatives or sustained release formulations thereof for treating Alzheimer's disease (AD).

Preferably, the composition for treating Alzheimer's disease or a related disorder in a subject in need thereof, comprises at least one of the following drug combinations for combined, separate or sequential administration:
phenformin and zonisamide,
phenformin and acamprosate,
phenformin and sulfisoxazole,
acamprosate and sulfisoxazole,
zonisamide and sulfisoxazole,
acamprosate and cilostazol,
acamprosate and zonisamide,
zonisamide and dyphylline,
zonisamide and argatroban,
phenformin and dyphylline,
phenformin and cilostazol,
tadalafil and cilostazol,
zonisamide and cilostazol,
phenformin and tadalafil, or
zonisamide and terbinafine.

Preferred compositions for treating Alzheimer's disease comprise zonisamide in combination with at least one compound chosen from the group consisting of dyphylline, tadalafil, argatroban, acamprosate, cinacalcet, terbinafine, cilostazol, baclofen, phenformin, amlodipine and sulfisoxazole, or salts or prodrugs or derivatives or sustained release formulations thereof.

In a most preferred embodiment, the composition according to the invention comprises at least zonisamide and acamprosate, or salts or prodrugs or derivatives or sustained release formulations thereof, for simultaneous, separate or sequential administration.

Other preferred compositions for treating Alzheimer's disease comprise phenformin, salts or prodrugs or derivatives or sustained release formulations thereof, either alone or in combination with at least one compound selected from the group of zonisamide, dyphylline, tadalafil, argatroban, acamprosate, cinacalcet, terbinafine, cilostazol, baclofen, amlodipine and sulfisoxazole, or salts or prodrugs or derivatives or sustained release formulations thereof.

In another embodiment, the composition further comprises at least one drug that modulates synapse function, for combined, separate or sequential use.

Preferably, the additional drug that modulates synapse function is selected from an inhibitor of ABAT (preferably, vigabatrin); and/or an inhibitor of ABL1, (preferably imatinib); and/or a modulator of ADORA2B (preferably dyphylline); and/or a modulator of AMPK (preferably, phenformin) and/or an inhibitor of CACNA1C, (preferably amlodipine); and/or an inhibitor of CACNA2D3, (preferably pregabalin); and/or a modulator of CASR (preferably, cinacalcet) ; and/or a modulator of CNGB3 (preferably, amiloride), and/or an inhibitor of DHFR (preferably, triamterene), and/or an inhibitor of EPHA3 (preferably, dasatinib), and/or antagonist of EDNRA endothelin receptor (preferably, sulfisoxazole), and/or a modulator of GABBR2 and glutamatergic receptors (preferably selected from baclofen and acamprosate), and/or a modulator of GABRA2 (preferably selected from phenobarbital and aztreonam), and/or an antagonist of GRIK1 (preferably, topiramate), and/or a modulator of GRIN2B and GRIN3A (preferably, acamprosate), and/or a modulator of HTR1B and HTR1D (preferably selected from ergotamine and eletriptan), and/or an antagonist of KCND2 (preferably, lidocaine), and/or a modulator of KCNMA1 (preferably, chlorzoxazone), and/or a modulator of NOS1 (preferably selected from ketotifen and propylthiouracil), and/or an inhibitor of NRP2 (preferably, pegaptanib), and/or a modulator of OPCML (preferably, alfentanil), and/or a modulator of OPRK1 (preferably selected from buprenorphine and pentazocine), and/or an inhibitor of trombin receptor PAR1 (preferably, argatroban), and/or an inhibitor of PDE11A and PDE4A, PDE5A phosphodiesterases (preferably, tadalafil), and/or an inhibitor of PDE3A/3B and PDE4A/4B phosphodiesterases and an activator of BK channels (preferably, cilostazol), and/or an inhibitor of PDE4D (preferably, milrinone), and/or an activator of PRKG1 (preferably selected from nitroprusside, tadalafil and cilostazol), and/or a modulator of RHOA (preferably selected from alendronate and terbinafine), and/or an inhibitor of sodium channel SCN1A and an activator of BK channels (preferably, zonisamide), and/or an inhibitor of SCN1A/B (preferably, fosphenytoin), and/or an inhibitor of SLC6A1 (preferably, tiagabine), and/or a modulator of SLC9A1 (preferably, buclizine), and/or an inhibitor of SLC12A1 (preferably, bumetanide), and/or an inhibitor of TROMBIN (preferably, desirudin), and/or a modulator of TSPO (preferably selected from flunitrazepam and temazepam), and/or an inhibitor of YES1 (preferably, dasatinib).

In other embodiments, said additional drug that modulates synapse function is selected from the drug or drugs that bind to or modulate the activity of a protein encoded by a gene selected from: ABAT, ABI1, ABL1, ADORA2A, ADORA2B, AKT, AMPK, ANKRA, APBA1, ARHGAP26, ATG5, BASSOON, BDNF, BECLIN1, BIN1, BK channels (KCNMA1, KCNMB1), CACNA1C, CACNA2D3, CACNA2D4, CADPS2, CALCINEURIN, CALMODULIN, CASK, CASR, CAST, CBL, CDC2, CDC42, CDC42BPB, CDC42EP3, CDH13, CDH2, CDK5, CITRON, CNGB3, CORTACTIN, CRAM, CREB, CRMP, CTNNB1, DAB1, DCC, DEPDC2, DHFR, DLG2, DYN1, DYN3, EDNRA, ENDOPHILIN, EPHA3, EPHBR, EPHEXIN, EPHRINA, EPHRINB, ERBB4, ERK1, ERK2, FES, FYN, GABBR1, GABBR2, GABRA2, GABRG2, GAT1, GLRA1, GEPHYRIN, GIPC1, GIPC2, GLUD1, GRANUPHILIN, GRIA2, GRIA3, GRID1, GRID2, GRIK1, GRIK2, GRIN2B, GRIN3A, GRIP, GRM3, GRM5, GRM6, GRM7, GRM8, HOMER, HTR1B, HTR1D, KALIRIN, KCNA2, KCHIP1, KCHIP2.2, KCND2, KCNJ3, KCNJ12, KTN1, KYNU, LYN, MAML3, MINT1, MUC1, MUNC13, MUNC18A, MYO6, MYOL, NAV1, NBEA, NCAM1, NCK1, NCK2, NETRIN1, NFKB1, NGEF, NGF, NGFR, NIL16, NLGN1, NOC2, NOS1, NOTCH1, NOTCH2, NOTCH3, NPC1, NPC2, NPIST, NRG3, NRP1, NRP2, NRX3, NTF3, NTF5, NWASP, OPCML, OPRK1, PAK6, PAK7, PAR1, PARK2, PDE11A, PDE3A/3B, PDE4A/4B/4D, PI3K, PIAS1, PICALM, PICK1, PIP5K, PKA, PKCA, PLD2, PLEXA1, PP1C, PPFIBP1, PRKG1, PSD95, PTN, PTPRF, PYK2, RAB3B, RABPHILIN, RAC1, RAP1, RAS, RASGRF2, RBPJ, REELIN, RGNEF, RHOA, RHOG, RIM2, RIMS1, RIMS2, ROBO2, ROCK2, RPH3AL, SACM1L, SAPAP, SCN1A, SCN1B, SEC24D, SEMA3A, SEMA3C, SEMA3E, SEMA4C, SIAH1A, SLC12A1, SLC12A2, SLC12A5, SLC1A2, SLC6A1, SLC6A18, SLC9A1, SLIT1, SNAP25, SORBS2, SRC, SRGAP3, STX2, STXBP6, SUM1, SV2C, SYNAPTOJANIN, SYNTAXIN1A, SYT12, TACE, TBR1, TRIO, TRKB, TROMBIN, TSPO, UBE2A, ULK4, UNC13C, UNC5C, VAMP2, VAMP5, VELI, VINCULIN, WASPIP, WAVE, WWOX, YAP, and YES1.

The inventors have established that the above drugs and drug combinations provide improved and synergistic biological effect leading to an effective correction or normalization or functional dysregulation leading to AD and related disorders.

The above named compounds are listed in the following table 1, together with their CAS number. As discussed before, it should be understood that the invention encompasses the use of the above compounds as well as any pharmaceutically acceptable salt, hydrate, ester, ether, isomers, racemate, conjugates, or pro-drugs thereof. Prodrugs may be prepared (e.g., by coupling the drug to a suitable carrier) to offer a better control over the pharmacokinetic parameters of the treatment.

TABLE 1

| DRUG NAME | CAS NUMBER |
|---|---|
| Acamprosate | 77337-76-9 |
| Alendronate | 66376-36-1 |
| Alfentanil | 71195-58-9 |
| Amiloride | 2016-88-8 |
| Amlodipine | 88150-42-9 |
| Argatroban | 74863-84-6 |
| Aztreonam | 78110-38-0 |
| Baclofen | 1134-47-0 |
| Balsalazide | 80573-04-2 |
| Buclizine | 82-95-1 |
| Bumetanide | 28395-03-1 |
| Buprenorphine | 52485-79-7 |
| Lidocaine | 137-58-6 |
| Chlorzoxazone | 95-25-0 |
| Cilostazol | 73963-72-1 |
| Cinacalcet | 226256-56-0 |
| Dasatinib | 302962-49-8 |
| Desirudin | 120993-53-5 |
| Dyphylline | 479-18-5 |
| Eletriptan | 143322-58-1 |
| Ergotamine | 113-15-5 |
| Flunitrazepam | 1622-62-4 |
| Fosphenytoin | 93390-81-9 |
| Imatinib | 152459-95-5 |
| Ketotifen | 34580-14-8 |
| Milrinone | 78415-72-2 |
| Nitroprusside | 15078-28-1 |
| Pegaptanib | 222716-86-1 |
| Pentazocine | 359-83-1 |
| Phenobarbital | 50-06-6 |
| Phenformin | 114-86-3 |
| Pregabalin | 148553-50-8 |
| Propylthiouracil | 51-52-5 |
| Sulfisoxazole | 127-69-5 |
| Tadalafil | 171596-29-5 |
| Temazepam | 846-50-4 |
| Terbinafine | 91161-71-6 |
| Tiagabine | 115103-54-3 |
| Topiramate | 97240-79-4 |
| Triamterene | 396-01-0 |
| Vigabatrin | 60643-86-9 |
| Zonisamide | 68291-97-4 |

Examples of pharmaceutically acceptable salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Additional examples of pharmaceutically acceptable inorganic or organic acid addition salts are listed in e.g., J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Therapy according to the invention may be performed alone or as drug combination, and/or in conjunction with any other therapy, targeting the same pathway or having distinct modes of actions. It and may be provided at home, the doctor's office, a clinic, a hospital's outpatient department, or a hospital, so that the doctor can observe the therapy's effects closely and make any adjustments that are needed.

In a particular embodiment, the compositions of this invention further comprise at least one drug that modulates angiogenesis, preferably that increases angiogenesis, for combined, separate or sequential use. More preferably, said at least one drug that modulates angiogenesis is selected from albuterol, alendronate, ambrisentan, aminocaproic acid, balsalazide, becaplermin, cabergoline, clopidogrel, dihydroergotamine, eplerenone, fenoldopam, fludrocortisone acetate, gemfibrozil, hesperetin, leflunomide, L-histidine, liothyronine, marimastat, meloxicam, mepacrine, methazolamide, methimazole, montelukast, netilmicin, nitroglycerin, phenylbutyrate, pyrimethamine, sunitinib, thiethylperazine, tirofiban, topotecan, vidarabine and warfarin (see table 2 below).

TABLE 2

| DRUG NAME | CAS NUMBER |
|---|---|
| Albuterol | 18559-94-9 |
| Alendronate | 66376-36-1 |
| Ambrisentan | 177036-94-1 |
| Aminocaproic acid | 60-32-2 |
| Balsalazide | 80573-04-2 |
| Becaplermin | 165101-51-9 |
| Cabergoline | 81409-90-7 |
| Clopidogrel | 113665-84-2 |
| Dihydroergotamine | 6190-39-2 |
| Eplerenone | 107724-20-9 |
| Fenoldopam | 67227-57-0 |
| Fludrocortisone | 127-31-1 |
| Gemfibrozil | 25812-30-0 |
| Hesperetin | 520-33-2 |
| Leflunomide | 75706-12-6 |
| L-histidine | 71-00-1 |
| Liothyronine | 6893-02-3 |
| Marimastat | 154039-60-8 |
| Meloxicam | 71125-38-7 |
| Mepacrine | 83-89-6 |
| Methazolamide | 554-57-4 |
| Methimazole | 60-56-0 |

TABLE 2-continued

| DRUG NAME | CAS NUMBER |
| --- | --- |
| Montelukast | 158966-92-8 |
| Netilmicin | 56391-56-1 |
| Nitroglycerin | 55-63-0 |
| Pyrimethamine | 58-14-0 |
| Sodium phenylbutyrate | 1716-12-7 |
| Sunitinib | 557795-19-4 |
| Thiethylperazine | 1420-55-9 |
| Tirofiban | 144494-65-5 |
| Topotecan | 119413-54-6 |
| Vidarabine | 24356-66-9 |
| Warfarin | 81-81-2 |

Alternatively, or in addition to the preceding embodiment, the compositions of this invention may further comprise at least one drug that modulates cell stress response, preferably that inhibits cell stress response, for combined, separate or sequential use.

The most preferred drugs that modulate cell stress response are selected from arabitol, mannitol, metaraminol, omeprazole, prilocaine, rapamycin, rifabutin, thioguanine and trehalose (see table 3 below).

TABLE 3

| DRUG NAME | CAS NUMBER |
| --- | --- |
| Arabitol | 488-82-4, 7643-75-6, 6018-27-5 |
| Mannitol | 69-65-8 |
| Metaraminol | 54-49-9 |
| Omeprazole | 73590-58-6 |
| Prilocaine | 721-50-6 |
| Rapamycin | 53123-88-9 |
| Rifabutin | 72559-06-9 |
| Thioguanine | 154-42-7 |
| Trehalose | 99-20-7 |

In a particular embodiment, the invention relates to a composition comprising a drug that ameliorates synapse function, a drug that increases angiogenesis, and a drug that inhibits cell stress response, for simultaneous, separate or sequential administration.

Other therapies used in conjunction with drug(s) or drug(s) combination(s) according to the present invention, may comprise one or more drug(s) that ameliorate symptoms of Alzheimer's disease or drug(s) that could be used for palliative treatment of Alzheimer's disease. Preferably, said one or more drug(s) is/are selected from 3APS, AAB-001, ABT-089, ABT-126, AC-3933, ACC-001, Acetaminophen, AFFITOPE AD01, AFFITOPE AD02, alpha-lipoic acid, alpha-tocopherol, AN1792, anti-Abeta, AQW051, Aripiprazole, Atomoxetine, Atorvastatin, AVE1625, AVP-923, AZD0328, AZD3480, Bapineuzumab, BAY94-9172 (ZK 6013443), Bifeprunox, Bioperine, BMS-708163, BRL-049653, Bryostatin, CAD106, Celecoxib, CERE-110, Cerebrolysin, CHF 5074, Choline, Circadin, Citalopram, Coenzyme Q, Copper, CTS21166, Curcumin, CX516 (Ampalex), CX717, Cyclophosphamate, DCB-AD1, Dextroamphetamine, DHA (Docosahexaenoic Acid), Digoxin, Dimebon (Latrepirdine), Divalproex, DMXB-A, Donepezil, Doxycycline, Egb 761, EHT 0202 tazolate, ELND005 (scyllo-inositol), EPAX 1050TG, Ergoloid mesylate, Epigallocatechin-Gallate, Escitalopram, Estradiol, Estrogen, Etanercept, EVP-6124, EVT101, Exelon, Fish oil, FK962, florpiramine F 18, Folate +Vitamin B6 +Vitamin B21, Gabapentin, Galantamine, Gemfibrozil, *Ginkgo biloba* extracts (for example EGb 761 or CP401), improved extracts of *Ginkgo biloba* (for example enriched in active ingredients or lessened in contaminant) or drug containing *Ginkgo biloba* extracts (for example Tanakan or Gingkor fort), Glucose, L-Glutamic Acid, GSI 136, GSI-953, GSK239512, GSK933776A, Haloperidol, HF0220, Huperzine A, hydrocodone/APAP, Ibuprofen, IFN-alpha2A, Indomethacin, Insulin, Intravenous Immunoglobulin, Ketasyn, Lecozotan, Leuprolide, Levodopa, Lipoic Acid, Lithium, Lorazepam, Lovostatin, Lutein, LY2062430 (solanezumab), LY2811376, LY450139, LY451395, MABT5102A, Malate, Masitinib (AB1010), Medroxyprogesterone, Melatonin, MEM 1003, MEM 3454, Memantine, Methylene blue, Methylphenidate, Mifepristone, MK0249, MK0677, MK0952, MK0952, MK3328, Modafinil, MPC-7869, NADH, Naproxen, Nefiracetam, Neptune Krill Oil, Neramexane, NICS-15, Nicoderm Patch, Nicotinamide (vitamin B3), Novasoy, NP031112, NS 2330, NSA-789, NSAIDs, Olanzapine, omega-3 polyunsaturated fatty acids (EPA+DHA), ONO-2506PO, Oxybate, Panax Ginseng, PAZ-417, PBT2, Perphenazine, PF-04360365, PF-04447943, PF-04494700, Phenserine, Phosphatidylserine, Pitavastatin, Posiphen, PPI-1019 (APAN), Pravastatin, Prazosin, Prednisone, Progesterone, PRX-03140, PYM50028, Quetiapine, R1450, Raloxifene, Ramipril, Rasagiline, Razadyne, resveratrol, rifampicin, risperidone, Rivastigmine, RN1219, R05313534, Rofecoxib, Rosiglitazone, Salvia officinalis (sage), SAM-315, SAM-531, SAM-760, SB-742457, Selenium, Sertraline, SGS-742, Simvastatin, SK-PC-B70M, Solanezumab, SR57667B, SRA-333, SRA-444, SSR180711C, ST101, T-817MA, Tacrine, Tarenflurbil, Testosterone, Tramiprosate (3APS), Trazodone, TRx0014 (methylthioninium chloride), Tryptophan, V950, Valproate, Varenicline, Vitamin C, Vitamin E, VP4896, Xaliproden, Zeaxanthin, Zolpidem, and ZT-1 (DEBIO-9902 SR).

The compositions of the invention typically comprise one or several pharmaceutically acceptable carriers or excipients. The duration of the therapy depends on the stage of the disease being treated, the combination used, the age and condition of the patient, and how the patient responds to the treatment.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recover from any as yet unforeseen side-effects. The drugs may also be formulated together such that one administration delivers all drugs.

The administration of each drug of the combination may be by any suitable means that results in a concentration of the drug that, combined with the other component, is able to correct the functioning of pathways implicated in AD.

While it is possible for the active ingredients of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and is may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Several drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The emulsifying agents may be naturally occurring gums (e.g., gum acacia or gum tragacanth).

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and duration of the treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

Administration can be one to several times daily for several days to several years, and may even be for the life of the patient. Chronic or at least periodically repeated long-term administration will be indicated in most cases.

Additionally, pharmacogenomic (the effect of genotype on the pharmacokinetic, pharmacodynamic or efficacy profile of a therapeutic) information about a particular patient may affect the dosage used.

Except when responding to especially impairing AD disease cases where higher dosages may be required, the preferred dosage of each drug in the combination usually lies within the range of doses not above those usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually no substantial effect. Accordingly, a particular advantage of the invention lies in the ability to use suboptimal doses of each compound, i.e., doses which are lower than therapeutic doses usually prescribed, preferably ½ of therapeutic doses, more preferably ⅓, ¼, ⅕, or even more preferably ¹/₁₀ to ¹/₁₀₀ of therapeutic doses. At such suboptimal dosages, the compounds alone would be substantially inactive, while the combination(s) according to the invention are fully effective.

A preferred dosage corresponds to amounts from 1% up to 50% of those usually prescribed for long-term maintenance treatment, for instance from 1% up to 10%.

Specific examples of dosages are provided below:
Zonisamide orally from 1 to 200 mg per day,
Dyphylline orally from 6 to 300 mg per day divided in two or three doses,
Tadalafil orally from 0.05 to 2.5 mg per day,
acamprosate orally from 1 to 50 mg per day,
cinacalcet orally from 0.3 to 15 mg per day,
terbinafine orally from 2.5 to 75 mg per day,
cilostazol orally from 1mg to 50 mg per day,
baclofen orally from 0.4 to 40 mg per day divided in two or three doses,
phenformin orally from 0.5 to 25 mg per day,
amlodipine orally from 0.05 to 5 mg per day,
sulfisoxazole orally from 0.4 to 4g per day divided in 6 to 4 doses.

Examples of dosages for combined therapies are provided below:
dasatinib orally from about 1 to 10 mg per day and acamprosate orally from about 7 to 70 mg three times daily,
aztreonam orally from about 20 to 1400 mg per day in 4 divided doses and tiagabine orally from about 0.3 to 3 mg per day,
chlorzoxazone orally from about 5 to 50 mg 3 or 4 times per day and tadalafil orally from about 0.05 to 0.5 mg per day,
chlorzoxazone orally from about 5 to 50 mg 3 or 4 times per day and cilostazol orally from about 1 to 10 mg per day,
chlorzoxazone orally from about 5 to 50 mg 3 or 4 times per day and terbinafine orally from about about 2.5 to 25 mg once or twice daily,
chlorzoxazone orally from about 5 to 50 mg 3 or 4 times per day and dasatinib orally from about 1 to 10 mg per day,
dasatinib orally from about 1 to 10 mg per day and terbinafine orally from about 2.5 to 25 mg once or twice daily,
cinacalcet orally from about 0.3 to 3 mg per day and acamprosate orally from about 7 to 70 mg three times daily,
aztreonam orally from about 20 to 1400 mg per day in 4 divided doses and vigabatrin orally from about 20 to 200 mg once or twice per day,
topiramate orally from about 2 to 60 mg per day and dyphylline orally from about 6 to 60 mg per day in two or three divided doses.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

I. Compounds prevent the toxicity of $A\beta_{25-35}$ Peptide

In this first series of experiments, candidate compounds have been tested for their ability to prevent or reduce the toxic effects of $A\beta_{25-35}$ peptide.

In AD, the protein forms aggregates of insoluble β-pleated sheets of fibrillar Abeta protein (amyloid). The conformational change from soluble to fibrillar forms seems to be a spontaneous event that is increased with higher concentrations of Abeta, so any production of larger amounts of Abeta than normal (or production of the larger, less soluble forms of Abeta) will tend to increase plaque formation. Once the Abeta plaque has started to form, other molecules can interact with the nascent plaque to produce eventually the mature plaque with its associated areas of neuronal cell death. Considering this, we have evaluated the effects of our candidate drugs on the viability of the cells exposed to the amyloid β protein.

Cell Culture

Primary rat cortical neurons are cultured as described by Singer et al., 1999. Briefly pregnant female rats of 15 days gestation are killed by cervical dislocation (Rats Wistar; Janvier) and the foetuses removed from the uterus. The cortex are removed and placed in ice-cold medium of Leibovitz (L15; Invitrogen) containing 1% of Penicillin-Streptomycin (PS; Invitrogen) and 1% of bovine serum albumin (BSA; Sigma). Cortex are dissociated by trypsinisation for 20 min at 37° C. (Trypsin EDTA 1×; Invitrogen) diluted in PBS without calcium and magnesium. The reaction is stopped by the addition of Dulbecco's modified Eagle's medium (DMEM; Invitrogen) containing DNAase I grade II (0.1 mg/ml; Roche Diagnostic) and 10% of foetal calf serum (FCS; Invitrogen). Cells are then mechanically dissociated by 3 passages through a 10 ml pipette. Cells are then centrifuged at 180×g for 10 min at 10° C. The supernatant is discarded and the cells of pellet are re-suspended in a defined culture medium consisting of Neurobasal (Invitrogen) supplemented with B27 (2%; Invitrogen), L-glutamine (0.2 mM;Invitrogen), 1% of PS solution and 10 ng/ml of Brain-derived neurotrophic factor (BDNF, Pan Biotech). Viable cells are counted in a Neubauer cytometer using the trypan blue exclusion test. Cells are seeded at a density of 30 000 cells/well in 96 well-plates (wells are pre-coated with poly-L-lysine (10 μg/ml; Sigma) and are cultured at 37° C. in a humidified air (95%)/CO2 (5%) atmosphere.

After 6 days of culture, cells are incubated with drugs (5 concentrations). After 1 hour, cells are intoxicated by 20 μM of beta-amyloïd (25-35; Sigma) in defined medium without BDNF but together with drugs. Cortical neurons are intoxicated for 2 days. BDNF (10 ng/ml) is used as a positive (neuroprotective) control. Two independent cultures are performed per condition, 6 wells per condition.

Neurites Length Quantification

Cells are fixed with a cool solution of ethanol (95%) and acetic acid (5%) for 10 min. After permeabilization with 0.1% of saponin, cells are blocked for 2 h with PBS containing 10% goat serum. Cells are then incubated with monoclonal antibody directed against the microtubule associated protein 2 (MAP-2; Sigma). This antibody reveals specifically cell bodies and neurites. The secondary antibody used is an Alexa Fluor 488 goat anti-mouse IgG (Molecular probe). Nuclei of neurons are revealed by a fluorescent dye (Hoechst solution, SIGMA). Twenty pictures are taken per well, using InCell Analyzer™ 1000 (GE Healthcare) at magnification 20×. All images are taken in the same conditions. Neurites length is quantified using Developer software (GE Healthcare).

Results

Figure 2:
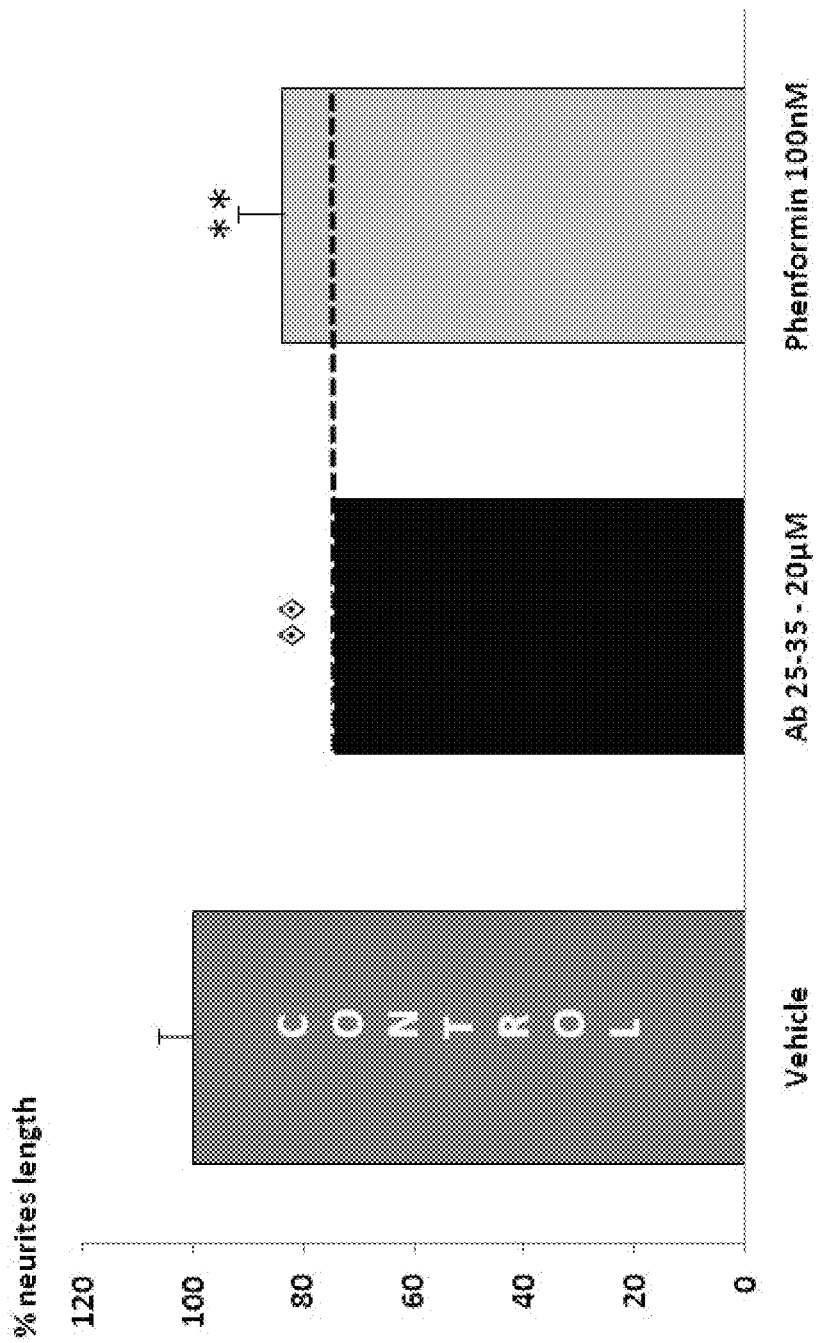
FIG. 2: Effect of phenformin on neurite outgrowth in beta-amyloid intoxicated rat primary cortical neuron culture. ◆◆: $p<0.01$: significantly different from vehicle. **:$p<0.001$: significantly different from $A\beta_{25-35}$. Bilateral Student's t test. $A\beta_{25-35}$ 20 µM produces a significant intoxication, above 25%, compared to vehicle-treated neurons. This intoxication is efficiently prevented by BDNF at 10 ng/ml (positive control). The intoxication is also significantly prevented by phenformin.

The results are presented in FIG. 1A, 1B, and 2. These results are extracted from two independent cultures, 6 wells per condition. All values are expressed as mean ±s.e. mean. A bilateral Student's t test analysis is performed on raw data. Results are expressed in percentage of neurites length, compared to the control (vehicle).

Drugs were incubated with rat primary cortical neurons one hour before Abeta$_{25\text{-}35}$ 20 μM intoxication that lasts 2 days (40).

Two days after this incubation the network of neurites length was quantified, reflecting axonal cell growth. The results clearly demonstrate a neuroprotective effect of the tested drugs of the invention against Abeta$_{25\text{-}35}$ intoxication (FIG. 1A, 1B, and FIG. 2).

II. Compounds and Combinations Thereof Prevent the Toxicity of Human Aβ$_{1\text{-}42}$ Peptide In this further series of experiments, candidate compounds have been tested for their ability to prevent or reduce the toxic effects of human Aβ$_{1\text{-}42}$. Aβ$_{1\text{-}42}$ is the full length peptide that constitutes aggregates found in biopsies from human patients afflicted with AD. The drugs are first tested individually, followed by assays of their combinatorial action. The effect is determined on various cell types, to further document the activity of the compounds.

II.1. Protection Against the Toxicity of Human Aβ$_{1\text{-}42}$ Peptide in Rate Primary Cortical Neuron Cells Test Compound and Human Amyloid-β1-42 Treatment Primary rat cortical neurons are cultured as described previously. Briefly, Aβ$_{1\text{-}42}$ peptide was reconstituted in define culture medium at 40 μM (mother solution) and was slowly shaked at +37° C. for 3 days in dark. The control medium was prepared in the same conditions.

After 3 days, the solution was used on primary cortical neurons as follows:

After 10 days of neuron culture, drug was solved in culture medium (+0.1% DMSO) and then pre-incubated with neurons for 1 hour before the Aβ$_{1\text{-}42}$ applications (in a final volume per culture well of 100 μl). One hour after drug incubation, 100 μl of Aβ$_{1\text{-}42}$ peptide was added to a final concentration of 10 μM diluted in presence of drug, in order to avoid further drug dilutions. Cortical neurons were intoxicated for 24 hours. Three separate cultures were performed per condition, 6 wells per condition.

BDNF (50 ng/ml) and Estradiol-β (100 and 150 nM) were used as positive control and reference compounds respectively. Three separate cultures will be performed per condition, 12 wells per condition.

Organization of Culture Plates

Estradiol-β at 100 and 150 nM were used as reference test compound and BDNF at 50 ng/ml was used as a positive control. Estradiol-β and BDNF were solved in culture medium and pre-incubated for 1 h before the amyloid-β$_{1\text{-}42}$ application.

The following conditions were assessed:
1 CONTROL PLAQUE: 12 wells/condition
Negative Control: medium alone +0.1% DMSO
Intoxication: amyloid-β$_{1\text{-}42}$ (10 μM) for 24 h
Positive control: BDNF (50 ng/ml) 1 hr followed by amyloid-β$_{1\text{-}42}$ (10 μM) for 24 h.
Reference compound: Estradiol (150 nM) 1hr followed by amyloid-β$_{1\text{-}42}$ (10 μM) for 24 h.
DRUG PLATE: 6 wells/condition
Negative Control: medium alone +0.1% DMSO
Intoxication: amyloid-β$_{1\text{-}42}$ (10 μM) for 24 h Drug 1: Drug 1—1 hr followed by amyloid-$\beta_{1-42}$ (10 μM) for 24 h Drug 2: Drug 2—1 hr followed by amyloid-$\beta_{1-42}$ (10 μM) for 24 h Lactate Dehydrogenase (LDH) Activity Assay 24 hours after intoxication, the supernatant was taken off and analyzed with Cytotoxicity Detection Kit (LDH, Roche Applied Science, ref: 11644793001, batch: 11800300). This colorimetric assay for the quantification of cell toxicity is based on the measurement of lactate dehydrogenase (LDH) activity released from the cytosol of dying cells into the supernatant.

Data Processing

All values are expressed as mean ±s.e.mean of the 3 cultures (n=6 per condition). Statistic analyses were done on the different conditions (ANOVA followed by the Dunnett's test when it was allowed, Statview software version 5.0).

Results

The results are presented in table 4 below and are exemplified in FIG. 3A, 3B, and 3C. These results clearly demonstrate a substantive effect of the drugs of the invention on $A\beta_{1-42}$-intoxicated neural cells.

TABLE 4

| DRUG NAME | Protective effect on $A\beta_{1-42}$ toxicity in neuronal cells |
|---|---|
| Baclofen (+/−) | + |
| Cinacalcet | + |
| Phenformin | + |
| Sulfisoxazole | + |
| Tadalafil | + |
| Zonisamide | + |

II.2. Protection Against the Toxicity of Human $A\beta_{1-42}$ Peptide on Human Brain Microvascular Endothelial Cells Ultrastructural studies have shown that brain microvessels are closely associated with β-amyloid plaques, and that Alzheimer's disease brain capillaries contain preamyloid deposits (42). Damage to the vasculature resulting from Abeta deposition can result in a reduction of cerebral blood flow (43). Moreover, Abeta peptides have been shown to be potent inhibitors of angiogenesis in vitro and in vivo (41). Aβ1-42 is the full length peptide that constitutes aggregates found in biopsies from human patients that suffered from AD. To be the closest as possible of the human disease, the protection afforded by candidate compounds toward Aβ1-42 was assessed.

We then chose to use Human Brain Microvascular Endothelial Cells (HBMEC) to further illustrate the protective effect of our compounds against the Aβ1-42 peptide injury. This model has been previously used to study the anti-angiogenic properties of mutant forms of Abeta peptide.

Human brain microvascular endothelial cerebral cells (HBMEC, ScienCell Ref: 1000, frozen at passage 10) were rapidly thawed in a waterbath at +37° C. The supernatant was immediately put in 9 ml Dulbecco's modified Eagle's medium (DMEM; Pan Biotech ref: PO4-03600) containing 10% of foetal calf serum (FCS; GIBCO ref 10270-106). Cell suspension was centrifuged at 180×g for 10 min at +4° C. and the pellets were suspended in CSC serum-free medium (CSC serum free, Cell System, Ref: SF-4Z0-500-R, Batch 51407-4) with 1.6% of Serum free RocketFuel (Cell System, Ref: SF-4Z0-500-R, Batch 54102), 2% of Penicillin 10.000 U/ml and Streptomycin 10 mg/ml (PS ; Pan Biotech ref: P06-07100 batch 133080808) and were seeded at the density of 20 000 cells per well in 96 well-plates (matrigel layer biocoat angiogenesis system, BD, Ref 354150, Batch A8662) in a final volume of 100 μl. On matrigel support, endothelial cerebral cells spontaneously started the process of capillary network morphogenesis (41). Three separate cultures were performed per condition, 6 wells per condition.

Candidate Compounds and Human Amyloid-$\beta_{1-42}$ Treatment

Briefly, Aβ1-42 peptide (Bachem, ref: H1368 batch 1010533) was reconstituted in define culture medium at 20 μM (mother solution) and was slowly shacked at +37° C. for 3 days in dark. The control medium was prepared in the same conditions. After 3 days, this human amyloid peptide was used on HBMEC at 2.5 μM diluted in control medium (optimal incubation time). The Aβ1-42 peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the $A\beta_{1-42}$ application (in a final volume per culture well of 100 μl). One hour after test compounds or VEGF incubation (two hours after cell seeding on matrigel), 100 μl of $A\beta_{1-42}$ peptide was added to a final concentration of 2.5 μM diluted in control medium in presence of test compounds or VEGF (in a 200 μl total volume/well), in order to avoid further drug dilutions.

Organization of Culuture Plates

VEGF-165, known to be a pro-angiogenic isoform of VEGF-A, was used for all experiments in this study as reference compound. VEGF-165 is one of the most abundant VEGF isoforms involved in angiogenesis. VEGF was used as reference test compound at 10 nM.

The following conditions were assessed:
Negative Control: medium alone +0.1% DMSO
Intoxication: amyloid-$\beta_{1-42}$ (2.5 μM) for 18 h
Positive control: VEGF-165 (10 nM) (1 reference compound/culture) 1 hr before the $A\beta_{1-42}$ (2.5 μM) addition for a 18 h incubation time.
Test compounds: Test compound 1 hr before the $A\beta_{1-42}$ (2.5 μM) addition for a 18 h incubation time.

Capillary Network Quantification

Per well, 2 pictures with 4× lens were taken using InCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

All values are expressed as mean ±s.e. mean of the 3 cultures (n=6 per condition). Statistic analyses were done on the different conditions performing an ANOVA followed by the Dunnett's test when it was allowed (Statview software version 5.0). The values (as %) inserted on the graphs show the amyloid toxicity evolution. Indeed, the amyloid toxicity was taken as the 100% and the test compound effect was calculated as a % of this amyloid toxicity.

Results

The results are shown in Table 5.

TABLE 5

| DRUG NAME | Protective effect in $A\beta_{1-42}$ intoxicated HBMEC cells |
|---|---|
| Baclofen (+/−) | + |
| Sulfisoxazole | + |
| Terbinafine | + |
| Zonisamide | + |
| Phenformin | + |

These results clearly show a protective effect of single drugs on human cells.

II.3. Effect of Combined Therapies on the Toxicity of Human $A\beta_{1-42}$ Peptide on Human HBMEC Cells and on Rat Primary Cortical Neurons We have also tested the efficacy of drug combinations of the invention in a human and rat system. The protocols used in these experiments are the same as described in sections II.1 and II.2 above.

Results

The following drug combinations are tested on human brain microvascular endothelial cells and on rat primary cortical neuron cells:
  phenformin and zonisamide,
  zonisamide and sulfisoxazole,
  acamprosate and zonisamide,
  zonisamide and dyphylline,
  zonisamide and argatroban,
  zonisamide and cilostazol,
  phenformin and acamprosate,
  phenformin and sulfisoxazole,
  acamprosate and sulfisoxazole,
  phenformin and dyphylline,
  phenformin and cilostazol,
  phenformin and tadalafil, and
  zonisamide and terbinafine.

All of the tested drug combinations give protective effect against toxicity of human $A\beta_{1-42}$ peptide in both models, as shown in Table 6 below.

TABLE 6

| DRUG NAME | Protective effect on $A\beta_{1-42}$ toxicity in neuronal cells | Protective effect in $A\beta_{1-42}$ intoxicated HBMEC cells |
|---|---|---|
| phenformin and zonisamide | + | + |
| zonisamide and sulfisoxazole | + | + |
| acamprosate and zonisamide | + | + |
| zonisamide and dyphylline | + | + |
| zonisamide and argatroban | + | + |
| zonisamide and cilostazol | + | + |
| phenformin and acamprosate | + | + |
| phenformin and sulfisoxazole | + | + |
| acamprosate and sulfisoxazole | + | + |
| phenformin and dyphylline | + | + |
| phenformin and cilostazol | + | + |

TABLE 6-continued

| DRUG NAME | Protective effect on $A\beta_{1-42}$ toxicity in neuronal cells | Protective effect in $A\beta_{1-42}$ intoxicated HBMEC cells |
|---|---|---|
| phenformin and tadalafil | + | + |
| zonisamide and terbinafine | + | + |

III. In Vivo Activity

Compounds and their combinations are tested in an in vivo model of Alzheimer disease. Overexpression of Alzheimer's disease -linked mutant human amyloid beta protein precursor (APP) transgenes has been the most reliable means of promoting deposition of Abeta in the brains of transgenic mice that served as AD disease models in numerous studies. As they age, these mutant APP mice develop robust amyloid pathology and other AD-like features, including decreased synaptic density, reactive gliosis, and some cognitive deficits. Many mutant APP mouse models show little evidence of overt neuronal loss and neurofibrillary tangle (NFT) pathology. Mice hemizygous for this BRI-Abeta42 transgene are viable and fertile with a normal lifespan. Transgenic BRI-Abeta42 mRNA is expressed in a pattern characteristic of the mouse prion protein promoter; highest transgene expression levels are detected in the cerebellar granule cells and hippocampus, followed by the cortex, pons, thalamus, and midbrain. In the transgenic fusion protein, Abetal-42 is fused to the C terminus of the BRI protein at the furin-like cleavage site such that cleavage results in efficient Abetal-42 secretion into the lumen or extracellular space. Therefore, these mice specifically express the Abetal-42 isoform. Hemizygous BRI-Abeta42 mice accumulate detergent-insoluble amyloid-beta with age and develop cored plaques in the cerebellum at as early as 3 months of age.

Development of forebrain pathology occurs later, extracellular Abeta plaques are not present consistently in the hippocampus and entorhinal/piriform cortices until 12 months of age. Amyloid beta deposits (cored plaques) can be observed as early as 3 months in molecular layer of cerebella of transgenic mice and becoming more pronounced with age; occasional extracellular plaques are seen in the entorhinal/piriform cortices and hippocampus at 6 months of age, but aren't consistently found until >12 months of age. Oldest mice show widespread pathology with cored and diffuse plaques in cerebellum, cortex, hippocampus, and olfactory bulb. Extracellular amyloid plaques show dense amyloid cores with radiating fibrils; many bundles of dystrophic neurites are observed at the periphery of these plaques. Reactive gliosis is associated with plaques.

Drug Treatments

The transgenic Tg (Prnp-ITM2B /APP695*42) A12E mc mice (31) has been obtained from Jackson Laboratory (http://jaxmice.jax.org/strain/007002.html). Mice founder with the highest Abeta42 plasma levels, line BRI-Abeta42A (12e), have been maintained on a mixed B6C3 background. Adult male transgenic mice have free access to food and water. In accord with an approved the Institutional Animal Care and Use Committee protocol, mice have been weighed and injected i.p. or force fed once daily for 10 to 20 consecutive weeks with either a control solution (placebo) or PXT drugs, prepared at different doses.

Survival Analysis

Survival rates have been analyzed using Kaplan-Meier methods. Holm-Sidak methods (post hoc) have been used for all pairwise multiple comparison tests. The extraneous deaths are censored. All comparisons have been made between littermates to limit any potentially confounding effects from background strain differences.

Behavioural Tests

Behavioural tests were designed and conducted according to the methods published by several authors (32-35).

Spatial Learning and Memory in the Morris Water Maze (MWM)

This experiment is performed in a circular pool, 90 cm in diameter, made of white plastic and filled with milky colored water. An escape platform, 8 cm in diameter, made of clear plastic was submerged 0.5 cm under the water level. Visual clues are provided by different geometrical forms printed in A4-sized letters and placed on the four surrounding walls (distance from the pool was from 50 to 70 cm). Each mouse has been given four trials daily (5- to 7-minute interval between trials, a total of 16 trials) for 4 days. Each trial has been performed from one of four different starting points. The movement of the mice is monitored using Videotrack Software (View Point). The time taken to locate the escape platform (escape latency; up to 60 seconds) has been determined. After locating the platform the mouse has been allowed to sit on it for 15 seconds. Mice who failed to find the platform within 60 seconds have been guided to it and allowed to stay on it for 15 seconds. A latency of 60 seconds is entered into the record for such an occurrence. All four trials per day have been averaged for statistical analysis, except for the first trial on day 1. On day 9 (5 days after the last training) mice have been subjected to a 60-second probe trial in which the platform is removed and the mice are allowed to search for it. The time that each animal spent in each quadrant has been recorded (quadrant search time). Several groups of male mice have been used at 3, 7, 10, and 12 months. The some few mice have showed freezing behaviour (eg, lying motionless in the water and refusing to swim) that strongly interfered with the test, these animals have been excluded from the data analysis. All behavioural tests are conducted under a quiet and light-reduced environment.

Working Memory Test in Radial Arm Water Maze

This cognitive-based sensitive measure of working memory has been obtained with the help of the apparatus consisted of a 100 cm-diameter waterfilled pool (also used for the Morris water maze and Platform Recognition tasks) fitted with an aluminium insert to create six radially-distributed swim arms. Testing consists of five, 1-min trials per daily session, for 9-12 consecutive days. At the start of each session, a clear submerged platform is positioned at the end of one of the six swim arms (randomly-selected, changed daily). For each of the first four acquisition trials, the animal is placed into one of the non-platform containing arms (randomized sequence) and allowed to search for the platform. During the 60 s trial, each time the animal enters another non-platform containing arm, it is gently returned to its starting location and an error recorded. After the fourth trial, the animal is allowed to rest for 30 min, followed by a fifth (retention) trial, which originates in the final non-platform containing swim arm.

The number of errors (incorrect arm choices) and escape latency (time to reach platform, maximum 60 s) are recorded for each trial.

Spatial Reference Learning and Memory in Circular Platform Test

This cognitive-based task test is performed with the help of the apparatus that consists of a 69 cm-diameter circular platform having 16 "escape" holes spaced equidistantly around the circumference. An escape refuge is installed beneath one of the holes, and a black curtain, on which are placed various visual cues, encircles the platform. The animal is placed in the center of the platform at the start of a single, 5 min trial and aversive stimuli (bright lights, fan wind) are presented. The total number of errors (head-pokes into non-escape holes) and escape latency (time to reach escape hole) are recorded.

Recognition Ability in Platform Recognition Test

This cognitive-based search task evaluates object identification and recognition ability. The target object consists of a 9 cm-diameter circular platform fitted with a 10 cm×40 cm black ensign, which is positioned 0.8 cm above the surface of the water in a 100 cm-diameter circular pool. Testing consists of four 60 s trials per day on each of four consecutive days. On each day, the target object is placed into a different quadrant of the pool for each trial, and the animal is released at the same location along the circumference of the pool for all four trials. The total latency (maximum 60 s) is recorded for each trial.

Modified Irwin Examination

A comprehensive screen, modified from Irwin is used to determine whether any of the mice exhibited physiological, behavioural, or sensorimotor impairments related to their genotype. To explore motor skills, coordination, and muscle strength, the mice are placed on a wire that was tightened between two 30-cm-high columns and their ability to balance on the wire is assessed. In addition, their ability to grasp and hang on the wire with all four paws for at least 5 seconds and to climb back on the wire is determined.

Quantification of Vascular Amyloid Deposition

For quantification of cerebral amyloid angiopathy (CAA), 5 μm paraffin-embedded sections at 30 μm intervals through the parietal or cerebellar cortex leptomeninges are immunostained with biotinylated-Ab9 antibody (anti-Aβ1-16, 1:500) overnight at 4° C. (n=5-7 mice per genotype at each age group, n=6 sections per mouse). Positively stained blood vessels are visually assessed using modified Vonsattel's scoring system (36) The CAA severity score is calculated by multiplying the number of CAA vessels with the CAA severity grade.

Histology: Immunohistochemistry and Immunofluorescence

Tg and WT mice from 3 to 12 months are anesthetized and transcardially perfused sequentially with 0.9% NaCl and 4% paraformaldehyde in 0.1 mol/L phosphatebuffered saline (PBS) (pH 7.4) or 10% formalin and 4% paraformaldehyde in 0.1 mol/L PBS (pH 7.4). Brains and spinal cords are removed and stored in 4% paraformaldehyde. Some samples are embedded in paraffin and cut on a sliding microtome at a thickness of 10 µm. Cryosections (14 µm) are cut on a cryostat and mounted on chrome alum-coated slides. Endogenous peroxidase is quenched by treating the section with methanol containing 0.3% H2O2 for 30 minutes. Sections are blocked in 10% horse serum. Primary antibodies are used and incubated overnight at 4° C. in the presence of 1% horse serum. All secondary biotinylated or fluorescein-, Texas Red-, and AMCA-coupled antibodies, fluorochromes, ABC-kit, and 3,3'-diaminobenzidine as chromogen for peroxidase activity are from Vector Laboratories. Incubation with the secondary antibody is held at room temperature for 1 hour. All washing steps (3 - 10 minutes) and antibody dilution are performed using phosphate-buffered saline (0.1 mol/L PBS, pH 7.4) or Tris-buffered saline (0.01 mol/L Tris, 0.15 mol/L NaCl, pH 7.4). Incubation with the ABC complex and detection with 3,3'-diaminobenzidine is carried out according to the manufacturer's manual. Hematoxylin counterstaining is performed according to standard procedures. A minimum of three mice per genotype, age, and sex is used for each determination (37).

Preparation of Brain Extracts

Brains are rapidly harvested over ice between 90 and 120 min after the final injection and frozen to −80° C. The right cerebral hemisphere from each mouse is weighed after freezing. Analysis of hemisphere mass by median absolute deviation allows us to exclude samples that are beyond 4 median absolute deviations from the rest of the set. Cerebral hemispheres are homogenized, and cell lysates containing whole protein are prepared according to the manufacturer's instructions for enzymatic assay kits (R&D Systems, Inc.). In brief, the brain cortices are homogenized in 800 µl of low salt containing 1x extraction buffer (R&D kit) and incubated on ice for 10 min. The homogenates are then centrifuged at 13,000 g for 15 min at 4° C. The protein concentration in each sample is estimated according to biuret-derived assay (Pierce). Levels of APP, Aβ40, and Aβ42 are measured by Western immunoblotting and sandwich ELISA techniques, respectively, as described (28). In addition, activities of α, β-, and γ-secretases may be measured from the same extracts.

Assay of Levels of Total APP in Mouse Cerebral Cortex Extracts

An equal-protein amount of brain extracts is loaded in each gel, 30 µg per lane per sample. Each gel contained eight treatments: control; drug1 7.5 mg/kg dose; and drug 2 in several doses. To minimize intra-gel variation, each gel contained three sets of all treatment groups. Each blot is probed with 22C11 antibody. Each blot is also probed with the β-actin antibody for normalization to transfer efficiency. The intensity of APP band signal is normalized with that of β-actin. Two sample "controls" are loaded in each gel/blot to test for blot to blot variation. Analysis of blots is performed in two ways: blot wise (n=3), to test for gel to gel variation; and combined blots (n=9 or 10) as described (38-39). Blot-wise analysis with n=3 shows the same trend as the final analysis with n=9 or 10 does. Results of the combined analysis are presented.

Aβ Sandwich ELISA

For brain Aβ ELISAs, forebrain and hindbrain Aβ levels are determined independently, and the olfactory bulb is excluded from analysis. For plasma Aβ analysis, blood is collected in EDTA-coated tubes after cardiac puncture. Blood samples are centrifuged at 3000 rpm for 10 min at 4° C., and the plasma is aliquoted and stored at −80° C. until used. Aβ levels are determined by end-specific sandwich ELISAs using Ab9 (anti-Aβ1-16 Ab) as the capture Ab for Aβ40, 13.1.1-HRP (anti-Aβ35-40 Ab) as the detection Ab for Aβ40, 2.1.3 (anti-Aβ35-42 Ab) as the capture Ab for Aβ42, and Ab9-HRP as the detection Ab for Aβ42 (n=5-7 mice per genotype at each age group). Aβ levels are normalized to the previous results using the same sets of mice as internal controls to minimize potential ELISA variability, as described (28).

Western Blotting

Snap-frozen forebrain samples are homogenized in radio-immunoprecipitation assay (RIPA) buffer (Boston BioProducts, Worcester, Mass.) with 1% protease inhibitor mixture (Roche). The homogenate is centrifuged at 100,000×g for 1 h at 4° C. Protein concentration in supernatants is determined using the BCA protein assay (Pierce). Protein samples (20 µg) are run on Bis-Tris 12% XT gels or Bis-Tris 4-12% XT gels (Bio-Rad, Hercules, Calif.) and transferred to 0.2 µm nitrocellose membranes. Blots are microwaved for 2 min in 0.1 M PBS twice and probed with Ab 82E1 (anti-Aβ1-16, 1:1000; IBL, Gunma, Japan) and anti-APP C-terminal 20 amino acids (1:1000) as described (28). Blots are stripped and reprobed with anti β-actin (1:1000; Sigma) as a loading control. Relative band intensity is measured using ImageJ software.

Quantification of Parenchymal Amyloid Deposition

Hemibrains are immersion fixed in 10% formalin and processed for paraffin embedding. Brain tissue sections (5 µm) were immunostained with anti-total Aβ antibody (Ab). Sections are counterstained with hematoxylin. Six sections per brain through the hippocampus, piriform cortex (bregma, −1.70 to −2.80 mm), or cerebellum (paraflocculus, crus ansiform, and simple lobules; bregma, −5.40 to −6.36 mm) are used for quantification (n=5-7 mice per genotype at each age group). The Aβ plaque burden is determined using MetaMorph software (Molecular Devices, Palo Alto, Calif.). For quantification of cored plaques, serial sections of those analyzed for A13 burden are stained with thioflavine S (ThioS), and the number of ThioS-positive plaques in the hippocampus, entorhinal/piriform cortex, or the cerebellum is counted. All of the above analyses are performed in a blinded manner.

Statistical Analysis of in vivo Data

Results from all experiments are analyzed with STATISTICA 8.0 (Statsoft).

Aβ levels, amyloid plaque burden, and CAA severity are analyzed by using ANOVA with the post hoc Holm-Sidak multiple comparison test or two-tailed Student's t test. If the data set does not meet the parametric test assumptions, either the Kruskal-Wallis test followed by the post hoc Dunn's multiple comparison or the Mann-Whitney rank sum test is performed. To test whether the Aβ levels in the bitransgenic mice were consistent with an additive sum of Aβ levels in the single transgenic littermates, a multiple linear regression with no intercept test is used. All comparisons are made between littermates.

Drug response modelling is done excluding the control (0 mg/kg) samples. ED50 corresponds to the dose (mg/kg) required to induce a 50% of maximal drug-induced response in the experiments. It is calculated using the Hill equation model for the log of ED50.

BIBLIOGRAPHY

1. Crook R., Verkkoniemi A., et al. (1998). A variant of Alzheimer's disease with spastic paraparesis and unusual plaques due to deletion of exon 9 of presenilin 1. *Nat Med.* 4(4): 452-5.

2. Houlden H., Baker M., et al. (2000). Variant Alzheimer's disease with spastic paraparesis and cotton wool plaques is caused by PS-1 mutations that lead to exceptionally high amyloid-beta concentrations. *Ann Neurol.* 48(5): 806-8.

3. Kwok J. B., Taddei K., et al. (1997). Two novel (M233T and R278T) presenilin-1 mutations in early-onset Alzheimer's disease pedigrees and preliminary evidence for association of presenilin-1 mutations with a novel phenotype. *Neuroreport* 8(6):1537-42.

4. Verkkoniemi A., Kalimo H., et al. (2001). Variant Alzheimer disease with spastic paraparesis: neuropathological phenotype. *J Neuropathol Exp Neurol.* 60(5): 483-92.

5. Citron M. (2004). Strategies for disease modification in Alzheimer's disease. *Nat Rev Neurosci.* 5(9): 677-85.

6. Suh Y. H. and Checler F. (2002). Amyloid precursor protein, presenilins, and alpha-synuclein: molecular pathogenesis and pharmacological applications in Alzheimer's disease. *Pharmacol Rev.* 54(3): 469-525.

7. Blacker D., Albert M. S., et al. (1994). Reliability and validity of NINCDS-ADRDA criteria for Alzheimer's disease. The National Institute of Mental Health Genetics Initiative. *Arch Neurol.* 51(12): 1198-204.

8. Rossor M. N., Fox N. C., et al. (1996). Clinical features of sporadic and familial Alzheimer's disease. *Neurodegeneration.* 5(4): 393-7.

9. Glenner G. G., Wong C. W., et al. (1984). The amyloid deposits in Alzheimer's disease: their nature and pathogenesis. *Appl Pathol.* 2(6): 357-69.

10. Ballatore C., Lee V. M., et al. (2007). Tau-mediated neurodegeneration in Alzheimer's disease and related disorders. *Nat Rev Neurosci.* 8(9): 663-72.

11. Bell K. F. and Claudio Cuello A. (2006). Altered synaptic function in Alzheimer's disease. *Eur J Pharmacol.* 545(1): 11-21.

12. Hardy J. A. and Higgins G. A. (1992). Alzheimer's disease: the amyloid cascade hypothesis. *Science.* 256 (5054): 184-5.

13. Braak H. and Braak E. (1991). Neuropathological stageing of Alzheimer-related changes. *Acta Neuropathol.* 82(4): 239-59.

14. Golde T. E. (2005). The Abeta hypothesis: leading us to rationally-designed therapeutic strategies for the treatment or prevention of Alzheimer disease. *Brain Pathol.* 15(1): 84-7.

15. Hardy J. and Selkoe D. J. (2002). The amyloid hypothesis of Alzheimer's disease: progress and problems on the road to therapeutics. *Science.* 297(5580): 353-6.

16. Selkoe D. J. (2000). The genetics and molecular pathology of Alzheimer's disease: roles of amyloid and the presenilins. *Neurol Clin.* 18(4): 903-22.

17. Huang Y. Z., Won S., et al. (2000). Regulation of neuregulin signaling by PSD-95 interacting with ErbB4 at CNS synapses. *Neuron.* 26(2): 443-55.

18. Naruse S., Thinakaran G., et al. (1998). Effects of PS1 deficiency on membrane protein trafficking in neurons. *Neuron.* 21(5):1213-21.

19. Leeuwen F. N., Kain H. E., et al. (1997). The guanine nucleotide exchange factor Tiam1 affects neuronal morphology; opposing roles for the small GTPases Rac and Rho. *J Cell Biol.* 139(3):797-807.

20. Guan K. L. and Rao Y. (2003). Signalling mechanisms mediating neuronal responses to guidance cues. *Nat Rev Neurosci.* 4(12): 941-56.

21. Comeau M. R., Johnson R., et al. (1998). A poxvirus-encoded semaphorin induces cytokine production from monocytes and binds to a novel cellular semaphorin receptor, VESPR. *Immunity.* 8(4): 473-82.

22. Hall K. T., Boumsell L., et al. (1996). Human CD100, a novel leukocyte semaphorin that promotes B-cell aggregation and differentiation. *Proc Natl Acad Sci U S A.* 93(21): 11780-5.

23. Kolodkin A. L., Matthes D. J., et al. (1993). The semaphorin genes encode a family of transmembrane and secreted growth cone guidance molecules. *Cell.* 75(7): 1389-99.

24. Luo Y., Shepherd I., et al. (1995). A family of molecules related to collapsin in the embryonic chick nervous system. *Neuron.* 14(6): 1131-40.

25. Messersmith E. K., Leonardo E. D., et al. (1995). Semaphorin III can function as a selective chemorepellent to pattern sensory projections in the spinal cord. *Neuron.* 14(5): 949-59.

26. Brose K. and Tessier-Lavigne M. (2000). Slit proteins: key regulators of axon guidance, axonal branching, and cell migration. *Curr Opin Neurobiol.* 10(1): 95-102.

27. Le Gall M., De Mattei C., et al. (2008). Molecular separation of two signaling pathways for the receptor Notch. *Dev Biol.* 313(2): 556-67.

28. Lahiri D. K. et al. (2007) Experimental Alzheimer's Disease Drug Posiphen[(Phenserine] Lowers Amyloid-betaPeptide Levels in Cell Culture and Mice. Journal of Pharmacology and experimental therapeutics 320: 386-396.

29. P. J. Mitchell et al. (2007) A quantitative method for analysis of in vitro neurite outgrowth. Journal of Neuroscience Methods 164 350-362.

30. Sang Tae KIM, et al. (2006) Neuroprotective Effect of Some Plant Extracts in Cultured CT105-Induced PC12 Cells. *Biol. Pharm. Bull.* 29(10) 2021-2024.

31. McGowan E.,et al. (2005) Aβ42 Is Essential for Parenchymal and Vascular Amyloid Deposition in Mice. Neuron 47: 191-199.

32. Leighty R. E. et al. (2008) Use of artificial neural networks to determine cognitive impairment and therapeutic effectiveness in Alzheimer's transgenic mice. Journal of Neuroscience Methods 167: 358-366.

33. Ashe KH (2001) Learning and memory in transgenic mice modelling Alzheimer's disease. Learning and Memory 8: 301-308.

34. Carlson GA, et al. (1997) Genetic modification of the phenotypes produced by amyloid precursor protein overexpression in transgenic mice. Human Molecular Genetics 6:1951-1959.

35. Hsiao K, et al. (1996) Correlative memory deficits, Abeta elevation, and amyloid plaques in transgenic mice. Science 274: 99-102.

36. Greenberg S. M. and Vonsattel J. P. (1997) Diagnosis of cerebral amyloid angiopathy. Sensitivity and specificity of cortical biopsy. Stroke 28(7):1418-22.

37. Schindowski K. et al. (2006) Alzheimer's Disease-Like Tau Neuropathology Leads to Memory Deficits and Loss of Functional Synapses in a Novel Mutated Tau Transgenic Mouse without Any Motor Deficits. Am J Pathol. 169: 599-616.

38. Lahiri DK, et al. (2004)Dietary supplementation with melatonin reduces levels of amyloid beta-peptides in the murine cerebral cortex. *Journal of Pin.Res.* 36:224-231.

39. Basha MR, et al. (2005) The fetal basis of amyloidogenesis: exposure to lead and latent overexpression of amyloid precursor protein and beta-amyloid in the aging brain. *Journal of Neuroscince* 25: 823-829.

40. Singer C., Figueroa-Masot X., Batchelor R., and Dorsa D. Mitogen-activated protein kinase pathway mediates estrogen neuroprotection after glutamate toxicity in primary cortical neurons. J. Neuroscience, 1999, 19(7): 2455-2463.

41. Paris D, et al. (2005) Anti-angiogenic activity of the mutant Dutch A(beta) peptide on human brain microvascular endothelial cells. *Brain Res Mol Brain Res.* 136: 212-30.

42. Miyakawa T (1997) Electron microscopy of amyloid fibrils and microvessels. *Ann NY Acad Sci* 826: 25-34.

43. Smith EE, et al (2009) Beta-amyloid, blood vessels, and brain function. Stroke. 40: 2601-6.

The invention claimed is:

1. A method of treating Lewy body dementia, the method comprising administering to a subject in need thereof an effective amount of zonisamide, or a salt or a sustained release formulation thereof.

2. The method of claim 1, further comprising simultaneously, separately, or sequentially administering to a subject in need thereof at least one compound selected from the group of dyphylline, tadalafil, argatroban, acamprosate, cinacalcet, terbinafine, cilostazol, baclofen, phenformin, amlodipine and sulfisoxazole, or salts or sustained release formulations thereof.

3. The method of claim 1, further comprising simultaneously, separately, or sequentially administering to a subject in need thereof at least one drug that modulates synapse function.

4. The method of claim 1, further comprising simultaneously, separately, or sequentially administering to a subject in need thereof at least one drug that modulates angiogenesis.

5. The method of claim 1, further comprising simultaneously, separately, or sequentially administering to a subject in need thereof at least one drug that modulates cell stress response.

6. The method of claim 1, wherein the effective amount of zonisamide, or a salt or sustained release formulation thereof, is formulated with a pharmaceutically acceptable carrier or excipient.

7. The method of claim 1, wherein the effective amount of zonisamide, or a salt or sustained release formulation thereof, is repeatedly administered to the subject.

* * * * *